(12) United States Patent
Hamall et al.

(10) Patent No.: US 7,857,801 B2
(45) Date of Patent: Dec. 28, 2010

(54) DIAPER HAVING DEPLOYABLE CHASSIS EARS AND STRETCH WAISTBAND

(75) Inventors: Kenneth Michael Hamall, West Chester, OH (US); Gary Dean LaVon, Liberty Township, OH (US); Kevin Michael Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 824 days.

(21) Appl. No.: 11/728,127

(22) Filed: Mar. 23, 2007

(65) Prior Publication Data

US 2008/0234649 A1 Sep. 25, 2008

(51) Int. Cl.
*A61F 13/15* (2006.01)
(52) U.S. Cl. ............... 604/385.28; 604/385.29; 604/385.3; 604/385.24; 604/385.25
(58) Field of Classification Search ............ 604/385.28, 604/385.29, 385.3, 385.24, 385.25
See application file for complete search history.

(56) References Cited

U.S. PATENT DOCUMENTS

| | | | |
|---|---|---|---|
| 1,733,997 A | 10/1929 | Marr | |
| 1,734,499 A | 11/1929 | Marinsky | |
| 1,989,283 A | 1/1935 | Limacher | |
| 2,058,509 A | 10/1936 | Rose | |
| 2,271,676 A | 2/1942 | Bjornbak | |
| 2,450,789 A | 10/1948 | Frieman | |
| 2,508,811 A | 5/1950 | Best et al. | |
| 2,568,910 A | 9/1951 | Condylis | |
| 2,570,796 A | 10/1951 | Gross | |
| 2,570,963 A | 10/1951 | Mesmer | |
| 2,583,553 A | 1/1952 | Faure | |
| 2,705,957 A | 4/1955 | Mauro | |
| 2,788,786 A | 4/1957 | Dexter | |
| 2,798,489 A | 7/1957 | Behrman | |
| 2,807,263 A | 9/1957 | Newton | |
| 2,830,589 A | 4/1958 | Doner | |
| 2,890,700 A | 6/1959 | Lönberg-Holm | |
| 2,890,701 A | 6/1959 | Weinman | |
| 2,898,912 A | 8/1959 | Adams | |
| 2,931,361 A | 4/1960 | Sostsrin | |
| 2,977,957 A | 4/1961 | Clyne | |
| 3,207,158 A | 9/1965 | Yoshitake et al. | |
| 3,386,442 A | 6/1968 | Sabee | |

(Continued)

FOREIGN PATENT DOCUMENTS

DE 19732499 2/1999

(Continued)

OTHER PUBLICATIONS

PCT International Report, PCT/US2008/057489 dated Jun. 26, 2008.

*Primary Examiner*—Jacqueline Stephens
(74) *Attorney, Agent, or Firm*—Richard L. Alexander

(57) ABSTRACT

A disposable diaper including a chassis and an absorbent assembly. The chassis includes laterally opposing side flaps formed by laterally inwardly folded portions of the chassis and deployable chassis ears formed by other laterally inwardly folded portions of the chassis. Each chassis ear is held laterally inwardly folded until being released and unfolded laterally outward so as to project laterally outward beyond the adjacent side flap. An elastically extensible stretch waistband overlies portions of the laterally opposing chassis ears and extends laterally across the waist region between them.

20 Claims, 16 Drawing Sheets

U.S. PATENT DOCUMENTS

| | | |
|---|---|---|
| 3,561,446 A | 2/1971 | Jones |
| 3,572,342 A | 3/1971 | Lindquist et al. |
| 3,578,155 A | 5/1971 | Small et al. |
| 3,592,194 A | 7/1971 | Duncan |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,022,211 A | 5/1977 | Timmons |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,527,990 A | 7/1985 | Sigl |
| 4,578,702 A | 3/1986 | Campbell |
| 4,585,450 A | 4/1986 | Rosch et al. |
| 4,589,878 A | 5/1986 | Mitrani |
| 4,601,717 A | 7/1986 | Blevins |
| 4,606,964 A | 8/1986 | Wideman |
| 4,610,678 A | 9/1986 | Weisman et al. |
| 4,623,342 A | 11/1986 | Ito et al. |
| 4,636,207 A | 1/1987 | Buell |
| 4,641,381 A | 2/1987 | Heran et al. |
| 4,670,011 A | 6/1987 | Mesek |
| 4,670,012 A | 6/1987 | Johnson |
| 4,680,030 A | 7/1987 | Coates et al. |
| 4,681,581 A | 7/1987 | Coates |
| 4,690,463 A | 9/1987 | Hart |
| 4,690,680 A | 9/1987 | Higgins |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,781,711 A | 11/1988 | Houghton et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,019,072 A | 5/1991 | Polski |
| 5,021,051 A | 6/1991 | Hiuke |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | DesMarais et al. |
| 5,269,775 A | 12/1993 | Freeland et al. |
| 5,312,386 A | 5/1994 | Correa et al. |
| 5,358,500 A | 10/1994 | Lavon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,415,644 A | 5/1995 | Enloe |
| 5,476,458 A | 12/1995 | Glaug et al. |
| 5,509,915 A | 4/1996 | Hanson |
| 5,518,801 A | 5/1996 | Chappell et al. |
| 5,531,730 A | 7/1996 | Dreier |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |

| | | | | | | |
|---|---|---|---|---|---|---|
| 5,622,589 | A | 4/1997 | Johnson et al. | 6,402,731 B1 | 6/2002 | Suprise et al. |
| 5,624,424 | A | 4/1997 | Saisaka et al. | 6,410,820 B1 | 6/2002 | McFall et al. |
| 5,625,222 | A | 4/1997 | Yoneda et al. | 6,413,249 B1 | 7/2002 | Turi et al. |
| 5,626,571 | A | 5/1997 | Young et al. | 6,419,667 B1 | 7/2002 | Avalon et al. |
| 5,635,191 | A | 6/1997 | Roe et al. | 6,423,048 B1 | 7/2002 | Suzuki et al. |
| 5,643,243 | A | 7/1997 | Klemp | 6,432,098 B1 | 8/2002 | Kline et al. |
| 5,643,588 | A | 7/1997 | Roe et al. | 6,432,099 B2 | 8/2002 | Rönnberg |
| H1674 | H | 8/1997 | Ames et al. | 6,443,933 B1 | 9/2002 | Suzuki et al. |
| 5,662,638 | A | 9/1997 | Johnson et al. | 6,461,342 B1 | 10/2002 | Tanji et al. |
| 5,674,215 | A | 10/1997 | Ronnberg | 6,461,343 B1 | 10/2002 | Schaefer et al. |
| 5,685,874 | A | 11/1997 | Buell et al. | 6,475,201 B2 | 11/2002 | Saito et al. |
| 5,691,035 | A | 11/1997 | Chappell et al. | 6,494,872 B1 | 12/2002 | Suzuki et al. |
| 5,695,488 | A | 12/1997 | Sosalla | 6,494,873 B2 | 12/2002 | Karlsson et al. |
| 5,723,087 | A | 3/1998 | Chappell et al. | 6,520,947 B1 | 2/2003 | Tilly et al. |
| 5,749,866 | A | 5/1998 | Roe et al. | 6,524,294 B1 | 2/2003 | Hilston et al. |
| 5,752,947 | A | 5/1998 | Awolin | 6,547,774 B2 | 4/2003 | Ono et al. |
| 5,772,825 | A | 6/1998 | Schmitz | 6,570,056 B1 | 5/2003 | Tanzer et al. |
| 5,776,121 | A | 7/1998 | Roe et al. | 6,572,601 B2 | 6/2003 | Suprise et al. |
| 5,779,831 | A | 7/1998 | Schmitz | 6,572,602 B2 | 6/2003 | Furuya et al. |
| 5,797,894 | A | 8/1998 | Cadieux et al. | 6,574,602 B1 | 6/2003 | Absar et al. |
| 5,810,800 | A | 9/1998 | Hunter et al. | 6,579,275 B1 | 6/2003 | Pozniak et al. |
| 5,814,035 | A | 9/1998 | Gryskiewicz et al. | 6,585,713 B1 | 7/2003 | LaMahieu et al. |
| 5,814,036 | A | 9/1998 | Ronnberg | 6,602,234 B2 | 8/2003 | Klemp et al. |
| 5,820,618 | A | 10/1998 | Roberts et al. | 6,605,070 B2 | 8/2003 | Ludwig et al. |
| 5,846,232 | A | 12/1998 | Serbiak et al. | 6,626,881 B2 | 9/2003 | Shingu et al. |
| 5,851,204 | A | 12/1998 | Mitzutani | 6,648,869 B1 | 11/2003 | Gillies et al. |
| 5,853,402 | A | 12/1998 | Faulks et al. | 6,648,870 B2 | 11/2003 | Itoh et al. |
| 5,865,823 | A | 2/1999 | Curro | 6,648,871 B2 | 11/2003 | Kusibojoska et al. |
| 5,865,825 | A | 2/1999 | Schlinz | 6,682,515 B1 | 1/2004 | Mizutani et al. |
| 5,873,868 | A | 2/1999 | Nakahata | 6,682,596 B2 | 1/2004 | Zehnder et al. |
| 5,876,391 | A | 3/1999 | Roe et al. | 6,689,115 B1 | 2/2004 | Popp et al. |
| 5,891,544 | A | 4/1999 | Chappell et al. | 6,706,028 B2 | 3/2004 | Roe et al. |
| 5,897,545 | A | 4/1999 | Kline et al. | 6,716,205 B2 | 4/2004 | Popp et al. |
| 5,904,673 | A | 5/1999 | Roe et al. | 6,726,792 B1 | 4/2004 | Johnson et al. |
| 5,931,825 | A | 8/1999 | Kuen et al. | 6,730,070 B2 | 5/2004 | Holmquist |
| 5,947,949 | A | 9/1999 | Inoue et al. | 6,755,808 B2 | 6/2004 | Balogh et al. |
| 5,951,536 | A | 9/1999 | Osborn, III et al. | 6,818,083 B2 | 11/2004 | Mcamish et al. |
| 5,957,908 | A | 9/1999 | Kline et al. | 6,840,930 B1 | 1/2005 | Miyamoto et al. |
| 5,968,029 | A | 10/1999 | Chappell et al. | 6,880,211 B2 | 4/2005 | Jackson et al. |
| 6,004,306 | A | 12/1999 | Robles et al. | 6,923,797 B2 | 8/2005 | Shinohara et al. |
| 6,022,430 | A | 2/2000 | Blenke et al. | 6,962,578 B1 | 11/2005 | LaVon |
| 6,022,431 | A | 2/2000 | Blenke et al. | 6,972,010 B2 | 12/2005 | Pesce et al. |
| 6,042,673 | A | 3/2000 | Johnson et al. | 7,013,941 B2 | 3/2006 | Schneider et al. |
| 6,102,892 | A | 8/2000 | Putzer et al. | 7,014,632 B2 | 3/2006 | Takino et al. |
| 6,107,537 | A | 8/2000 | Elder et al. | 7,014,649 B2 | 3/2006 | Bacher |
| 6,110,157 | A | 8/2000 | Schmidt | 7,037,299 B2 | 5/2006 | Turi et al. |
| 6,117,121 | A | 9/2000 | Faulks et al. | 7,048,726 B2 | 5/2006 | Kusagawa et al. |
| 6,117,803 | A | 9/2000 | Morman | 7,066,921 B2 | 6/2006 | Schmoker et al. |
| 6,120,486 | A | 9/2000 | Toyoda et al. | D525,706 S | 7/2006 | Pargass |
| 6,120,487 | A | 9/2000 | Ashton | 7,122,193 B1 | 10/2006 | Guichard |
| 6,120,489 | A | 9/2000 | Johnson et al. | 7,160,281 B2 | 1/2007 | LeMinh |
| 6,120,866 | A | 9/2000 | Arakawa et al. | 7,195,622 B2 | 3/2007 | Lindstrom |
| 6,129,720 | A | 10/2000 | Blenke et al. | 7,211,072 B2 | 5/2007 | Nawata et |
| 6,156,023 | A | 12/2000 | Yoshioka | 7,220,251 B2 | 5/2007 | Otsubo |
| 6,156,424 | A | 12/2000 | Taylor | 7,288,079 B2 | 10/2007 | Toyoshima et al. |
| 6,165,160 | A | 12/2000 | Suzuki et al. | 7,291,137 B2 | 11/2007 | LaVon et al. |
| 6,174,302 | B1 | 1/2001 | Kumasaka | 7,314,465 B2 | 1/2008 | Van Gompel et al. |
| 6,177,607 | B1 | 1/2001 | Blaney et al. | 7,318,820 B2 | 1/2008 | LaVon |
| 6,186,996 | B1 | 2/2001 | Martin | 7,320,684 B2 | 1/2008 | LaVon et al. |
| 6,210,390 | B1 | 4/2001 | Karlsson | 7,347,848 B2 | 3/2008 | Fernfors |
| 6,238,380 | B1 | 5/2001 | Sasaki | 7,435,244 B2 | 10/2008 | Schroer, Jr. et al. |
| 6,241,716 | B1 | 6/2001 | Rönnberg | 2002/0045881 A1 | 4/2002 | Kusibojoska et al. |
| 6,254,294 | B1 | 7/2001 | Muhar | 2002/0052588 A1 | 5/2002 | Otsubo |
| 6,306,122 | B1 | 10/2001 | Narawa et al. | 2002/0087139 A1 | 7/2002 | Popp |
| 6,312,420 | B1 | 11/2001 | Sasaki et al. | 2002/0099351 A1 | 7/2002 | Onishi et al. |
| 6,322,552 | B1 | 11/2001 | Blenke et al. | 2002/0138063 A1 | 9/2002 | Kuen |
| 6,325,787 | B1 | 12/2001 | Roe et al. | 2002/0151861 A1 | 10/2002 | Klemp |
| 6,334,858 | B1 | 1/2002 | Rönnberg et al. | 2002/0173767 A1 | 11/2002 | Popp et al. |
| 6,336,922 | B1 | 1/2002 | VanGompel et al. | 2003/0003269 A1 | 1/2003 | Lee et al. |
| 6,350,332 | B1 | 2/2002 | Thomas et al. | 2003/0088223 A1 | 5/2003 | Vogt et al. |
| 6,364,863 | B1 | 4/2002 | Yamamoto et al. | 2003/0088230 A1 | 5/2003 | Balogh et al. |
| 6,383,431 | B1 | 5/2002 | Dobrin | 2003/0089454 A1 | 5/2003 | Johnson |
| 6,402,729 | B1 | 6/2002 | Boberg et al. | 2003/0105447 A1 | 6/2003 | Widlund et al. |

| | | |
|---|---|---|
| 2003/0144644 A1 | 7/2003 | Murai et al. |
| 2003/0148694 A1 | 8/2003 | Ghiam |
| 2003/0233082 A1 | 12/2003 | Kline et al. |
| 2004/0022998 A1 | 2/2004 | Miyamoto et al. |
| 2004/0082928 A1 | 4/2004 | Pesce et al. |
| 2004/0122404 A1 | 6/2004 | Meyer et al. |
| 2004/0122411 A1 | 6/2004 | Hancock-Cooke |
| 2004/0127868 A1 | 7/2004 | Olson et al. |
| 2004/0147890 A1 | 7/2004 | Nakahata et al. |
| 2004/0162536 A1 | 8/2004 | Becker et al. |
| 2004/0167486 A1 | 8/2004 | Busam et al. |
| 2004/0225271 A1 | 11/2004 | Datta et al. |
| 2004/0236299 A1 | 11/2004 | Tsang et al. |
| 2004/0236304 A1 | 11/2004 | Coates et al. |
| 2004/0249355 A1 | 12/2004 | Tanio et al. |
| 2005/0004548 A1 | 1/2005 | Otsubo et al. |
| 2005/0038401 A1 | 2/2005 | Suzuki et al. |
| 2005/0085784 A1 | 4/2005 | LeMinh et al. |
| 2005/0131373 A1 | 6/2005 | Wright et al. |
| 2005/0137550 A1 | 6/2005 | Schmoker et al. |
| 2005/0171499 A1 | 8/2005 | Nigam et al. |
| 2005/0177126 A1 | 8/2005 | Kurata |
| 2005/0203475 A1 | 9/2005 | LaVon et al. |
| 2005/0203479 A1 | 9/2005 | Sakaguchi et al. |
| 2005/0288645 A1 | 12/2005 | LaVon |
| 2005/0288646 A1 | 12/2005 | LaVon |
| 2006/0264860 A1 | 11/2006 | Beck et al. |
| 2006/0264861 A1 | 11/2006 | LaVon et al. |
| 2006/0271010 A1 | 11/2006 | LaVon |
| 2006/0293637 A1 | 12/2006 | La Von et al. |
| 2006/0293638 A1* | 12/2006 | LaVon et al. ........... 604/385.28 |
| 2007/0032770 A1 | 2/2007 | LaVon et al. |
| 2007/0049897 A1 | 3/2007 | LaVon et al. |
| 2007/0066951 A1 | 3/2007 | LaVon et al. |
| 2007/0066952 A1 | 3/2007 | LaVon et al. |
| 2007/0118088 A1 | 5/2007 | LaVon |
| 2007/0118089 A1 | 5/2007 | LaVon |
| 2007/0144660 A1 | 6/2007 | O'Sickey et al. |
| 2007/0173780 A1 | 7/2007 | LaVon et al. |
| 2007/0173782 A1 | 7/2007 | LaVon |
| 2008/0183149 A1 | 7/2008 | LaVon et al. |
| 2008/0208155 A1 | 8/2008 | LaVon et al. |
| 2008/0208156 A1 | 8/2008 | LaVon et al. |

FOREIGN PATENT DOCUMENTS

| | | |
|---|---|---|
| EP | 0 206 208 | 12/1986 |
| EP | 374542 | 6/1990 |
| EP | 0 403 832 A1 | 12/1990 |
| EP | 0403832 | 12/1990 |
| EP | 0761194 | 3/1997 |
| EP | 0793469 | 9/1997 |
| EP | 0875226 | 4/1998 |
| EP | 0 893 115 | 1/1999 |
| EP | 0 916 327 A1 | 5/1999 |
| EP | 0951890 | 10/1999 |
| EP | 1224922 | 7/2002 |
| EP | 1384458 | 1/2004 |
| EP | 1447066 | 8/2004 |
| EP | 1447067 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 | 12/2001 |
| GB | 1307441 | 2/1973 |
| GB | 1 513 055 | 6/1978 |
| GB | 2 101 468 | 1/1983 |
| GB | 2 262 873 A | 7/1993 |
| JP | 04 122256 | 4/1992 |
| JP | 11-318980 | 11/1999 |
| WO | WO 8404242 | 11/1984 |
| WO | WO 95/16746 | 6/1995 |
| WO | WO 95/16746 A1 | 6/1995 |
| WO | WO 95/19753 | 7/1995 |
| WO | WO 95/29657 | 11/1995 |
| WO | WO 97/048357 | 12/1997 |
| WO | WO 98/16179 A1 | 4/1998 |
| WO | WO 99/13813 | 3/1999 |
| WO | WO 2004/105664 | 12/2004 |
| WO | WO 03/009794 | 2/2005 |
| WO | WO 2005/016200 | 2/2005 |
| WO | WO 2005/016211 | 2/2005 |
| WO | WO 2005/081937 | 9/2005 |
| WO | WO 2005/087164 | 9/2005 |
| WO | WO 2006/123976 | 11/2006 |
| WO | WO 2007/000315 | 1/2007 |
| WO | WO 2007/015224 | 8/2008 |

* cited by examiner

DIAPER HAVING DEPLOYABLE CHASSIS EARS AND STRETCH WAISTBAND

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increase in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

A disposable diaper includes a chassis and an absorbent assembly. The chassis includes laterally opposing side flaps formed by laterally inwardly folded portions of the chassis and deployable chassis ears formed by other laterally inwardly folded portions of the chassis. Each chassis ear is held laterally inwardly folded until being deployed by being released and unfolded laterally outward so as to project laterally outward beyond the adjacent side flap. Fastening elements may be disposed on at least two of the chassis ears, the fastening elements being adapted for fastening the front waist region to the back waist region to encircle a waist and legs of a wearer. An elastically extensible stretch waistband overlies portions of the laterally opposing chassis ears and extends laterally across the waist region between them. The absorbent assembly may be attached in a cruciform pattern to the chassis to allow portions of the chassis underlying the absorbent assembly and lying outside the cruciform attachment pattern to extend laterally.

BRIEF DESCRIPTION OF THE DRAWINGS

In the accompanying drawing figures, like reference numerals identify structurally corresponding elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence of absence of particular elements in any of the exemplary embodiments, except as may be delineated explicitly in the corresponding written description.

In the drawing figures and in the written description, lowercase letters appended to reference numerals indicate generally symmetric elements, e.g., left and right symmetric elements may be respectively identified by the reference numerals 1a and 1b. A reference numeral without an appended lowercase letter identifies all of the elements to which that particular reference numeral applies, e.g., the same elements as a group may be designated 1.

DETAILED DESCRIPTION OF THE INVENTION

Figure 1:
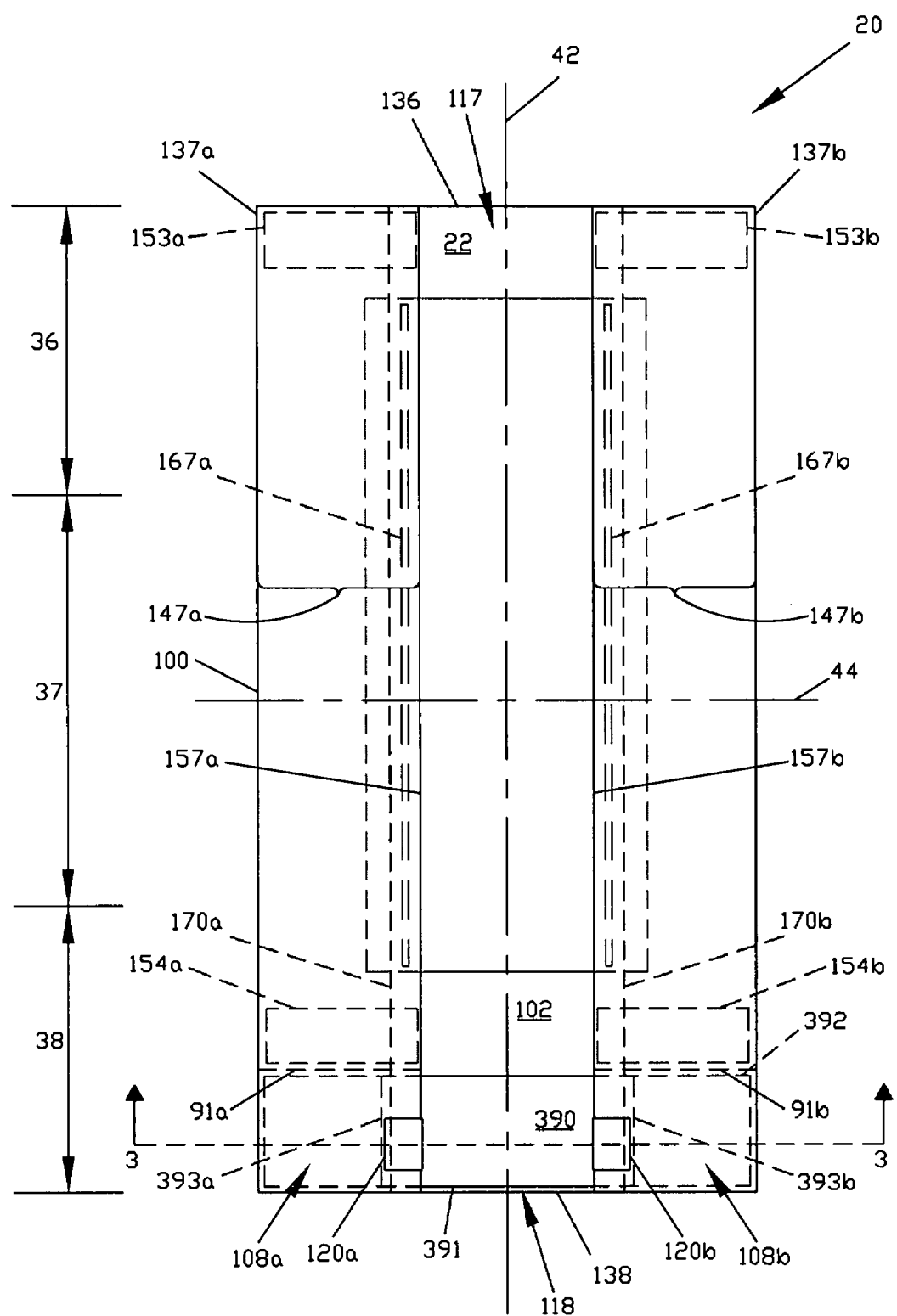
FIG. 1 is a plan view of an exemplary disposable absorbent article in the form of a diaper 20, which is shown in its flat, uncontracted state, i.e., without the contraction induced by elastic members. In this figure, the interior portion of the diaper 20 that faces inwardly toward the wearer and contacts the wearer is shown facing the viewer.

In this description, the following terms have the following meanings:

The term "absorbent article" refers to a device that absorbs and contains liquid, and more specifically, refers to a device that is placed against or in proximity to the body of a wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner. In this description, a disposable diaper is described as being representative of an exemplary disposable absorbent article.

The term "deploy" in all its forms refers to the manipulation of any disclosed deployable structural element from its initial configuration to a configuration in which it can be used for its intended purpose in the article on which it is provided.

The term "longitudinal" refers to a direction running from a waist edge to an opposing waist edge of the article and generally parallel to the maximum linear dimension of the article.

The term "lateral" refers to a direction running from a side edge to an opposing side edge of the article and generally at a right angle to the longitudinal direction.

The term "circumferential" refers to a direction encircling a portion or all of the waist of the wearer generally parallel to the lateral direction. This term is used particularly when describing the elements that extend around and form the margin of the waist opening.

The term "disposed" refers to an element being attached and positioned in a particular place or position in a unitary structure with other elements.

The term "attach" refers to elements being connected or united by fastening, adhering, bonding, etc. by any method suitable for the elements being attached together and their constituent materials. Many suitable methods for attaching elements together are well-know, including adhesive boding, pressure bonding, thermal bonding, mechanical fastening, etc. Such attachment methods may be used to attach elements together over a particular area either continuously or intermittently. Unless indicated otherwise, elements that are described as being attached to each other are attached directly together, with either nothing or only bonding material, e.g., an adhesive, between them. Unless indicated otherwise, elements that are described as being attached to each other are attached permanently together, i.e., attached in such a way that one or both of the elements and/or any bonding material that is present must be damaged in order to separate them. This permanent attachment excludes temporary attachment, such as by means of fasteners that may be unfastened.

The term "laminate" refers to elements being attached together in a layered arrangement.

The term "cohesive" refers to the property of a material that, once set, sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer of a layered structure through the thickness of which liquid water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the laterally proximal edge of a longitudinally extending element is located nearer to the longitudinal axis than laterally distal edge of the same element is located relative to the same longitudinal axis. When used to describe relative locations with respect to the axes, synonyms include "inboard" and "outboard", respectively.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

The term "nonwoven" refers to a sheet, web, or batt of directionally or randomly oriented fibers, made by bonding or entangling the fibers through mechanical, thermal, or chemical means. Nonwoven materials exclude paper and products which are woven, knitted, tufted, or felted by wet milling. The fibers are preferably but not necessarily man-made synthetics.

The term "stretch waistband" refers to a structural component that resist elongation by providing a contractive force around the waist opening of a diaper when it is expanded circumferentially, i.e., when the waist regions of the diaper are expanded laterally.

As can be seen in the drawing figures, one end portion of the exemplary diaper 20 is configured as a front waist region 36, the longitudinally opposing end portion is configured as a back waist region 38, and an intermediate portion is configured as a crotch region 37.

The basic structure of the diaper 20 includes a chassis 100, which has a laterally extending front edge 136, a longitudinally opposing back edge 138, laterally opposing side edges 137, an interior surface 102, and an exterior surface 104. A longitudinal axis 42 extends through the midpoints of the front edge 136 and the back edge 138 and a lateral axis 44 extends though the midpoints of the side edges 137. The exemplary chassis 100 shown in FIG. 1 additionally has longitudinally extending and laterally opposing side flaps 147 as well as laterally opposing chassis ears 106 and/or 108, which are described in more detail below.

The basic structure of the diaper 20 also includes an absorbent assembly 200 that is attached to the chassis 100. The absorbent assembly 200 absorbs and retains liquid bodily waste materials. The absorbent assembly 200 has a laterally extending front edge 236, a longitudinally opposing back edge 238, laterally opposing side edges 237, an interior surface 202, and an exterior surface 204. The absorbent assembly 200 may be disposed either symmetrically or asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically offset toward the front waist region 36 with respect to the lateral axis 44.

The edges of the absorbent assembly 200 may lie inward of the respective edges of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

When the diaper 20 is worn on the lower torso of a wearer, the front waist edge 136 and the back waist edge 138 encircle the waist of the wearer, while at the same time the chassis side edges 137 encircle the legs of the wearer, the crotch region 37 is generally positioned between the legs of the wearer, and the absorbent assembly 200 extends from the front waist region 36 through the crotch region 37 to the back waist region 38.

The basic structure of the diaper 20 also includes at least one stretch waistband that is attached to the chassis 100 in a waist region. When the chassis 100 is stretched in the circumferential direction, the stretch waistband resists by providing a contractive force around the waist opening of the diaper 20. For example, in FIG. 1, an interior back stretch waistband 390 is shown attached interiorly to the chassis 100 in the back waist region 38 of the diaper 20. This back stretch waistband 390 has a laterally extending longitudinally distal edge 391 and a longitudinally opposing laterally extending proximal edge 392.

Figure 16:
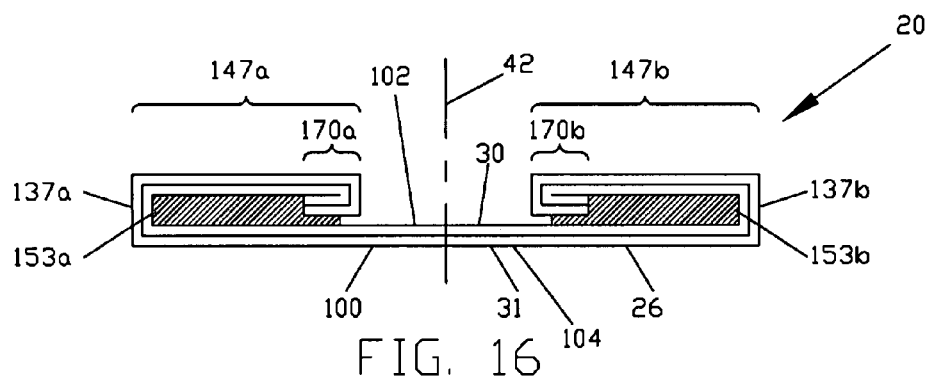
FIG. 16 is a section view of the diaper 20 of FIGS. 11 and 12 taken at the section line 16-16.

The chassis 100 include a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as laminates of a film and a nonwoven, are also well-known and may be suitable for use as the backsheet 26. Such a laminate backsheet may be oriented with the nonwoven 31 disposed exteriorly, as shown in FIG. 16, to provide the feel and appearance of a more cloth-like outermost layer than would be provided by using the film 30 as the outermost layer.

The chassis 100 may, but need not, additionally include an inner liner 22 attached to the backsheet 26. Such an inner liner 22 is preferably formed of a soft material that will not irritate the skin of the wearer. Many suitable materials for the inner liner 22 are well-known in the art, including rayon and synthetic nonwovens such as spunbonded or carded polypropylene, polyethylene, or polyester. An inner liner 22 may form a portion of the interior surface 102 of the chassis 100, such as in the respective front and back laterally central portions 117 and 118 between the edges 236 and 238 of the absorbent assembly 200 and the waist edges 136 and 138 of the chassis 100 and thereby server to isolate the skin of the wearer from a portion of the backsheet 26 as may be desirable, for example, when the diaper 20 is worn under conditions in which contact between the skin and a backsheet film could uncomfortable.

As shown in the figures, the exemplary chassis 100 has longitudinally extending and laterally opposing side flaps 147 that are disposed on the interior portion of the diaper 20 that faces inwardly toward the wearer and contacts the wearer. The side flaps 147 are formed by folding portions of the chassis 100 laterally inward, i.e., toward the longitudinal axis 42, to form both the respective side flaps 147 and the side edges 137 of the chassis 100, as shown in the figures Each side flap 147 has a proximal edge 157. In the exemplary diaper 20 shown in FIG. 1, the side flaps 147 overlap the absorbent assembly 200, i.e., their proximal edges 157 lie laterally inward of the respective side edges 237 of the absorbent assembly 200. Such an overlapped configuration may be desirable in order to impart a more finished appearance to the diaper 20 than that imparted by a non-overlapped configuration. Alternatively, the side flaps 147 may not overlap the absorbent assembly 200.

Figure 9:
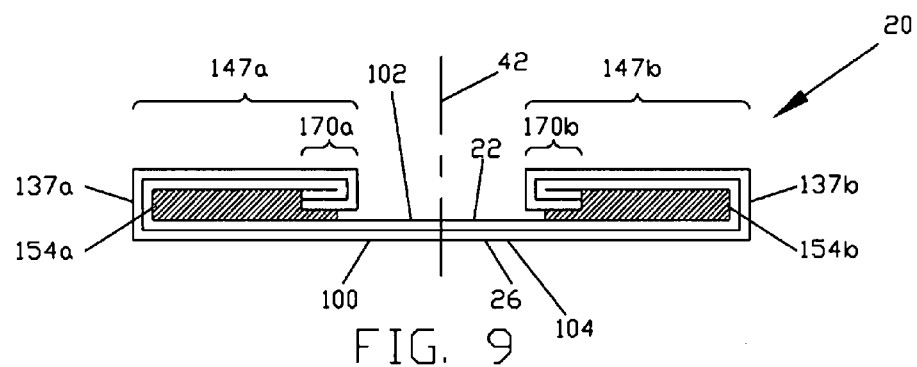
FIG. 9 is a section view of the diaper 20 of FIGS. 5 and 6 taken at the section line 9-9.

Each side flap 147 is attached to the interior surface 102 of the chassis 100 in an attachment zone 153 in the front waist region 36 and in a longitudinally opposing attachment zone 154 in the back waist region 38, as shown in detail in FIG. 9. In embodiments in which the front edge 236 or the back edge 238 of the absorbent assembly 200 coincides with the respective front waist edge 136 or back waist edge 138 of the chassis 100 and the side flaps 147 overlap the absorbent assembly 200, the side flaps 147 may be attached to the absorbent assembly 200 instead of, or in addition to, being attached to the interior surface 102 of the chassis 100.

Figure 10:
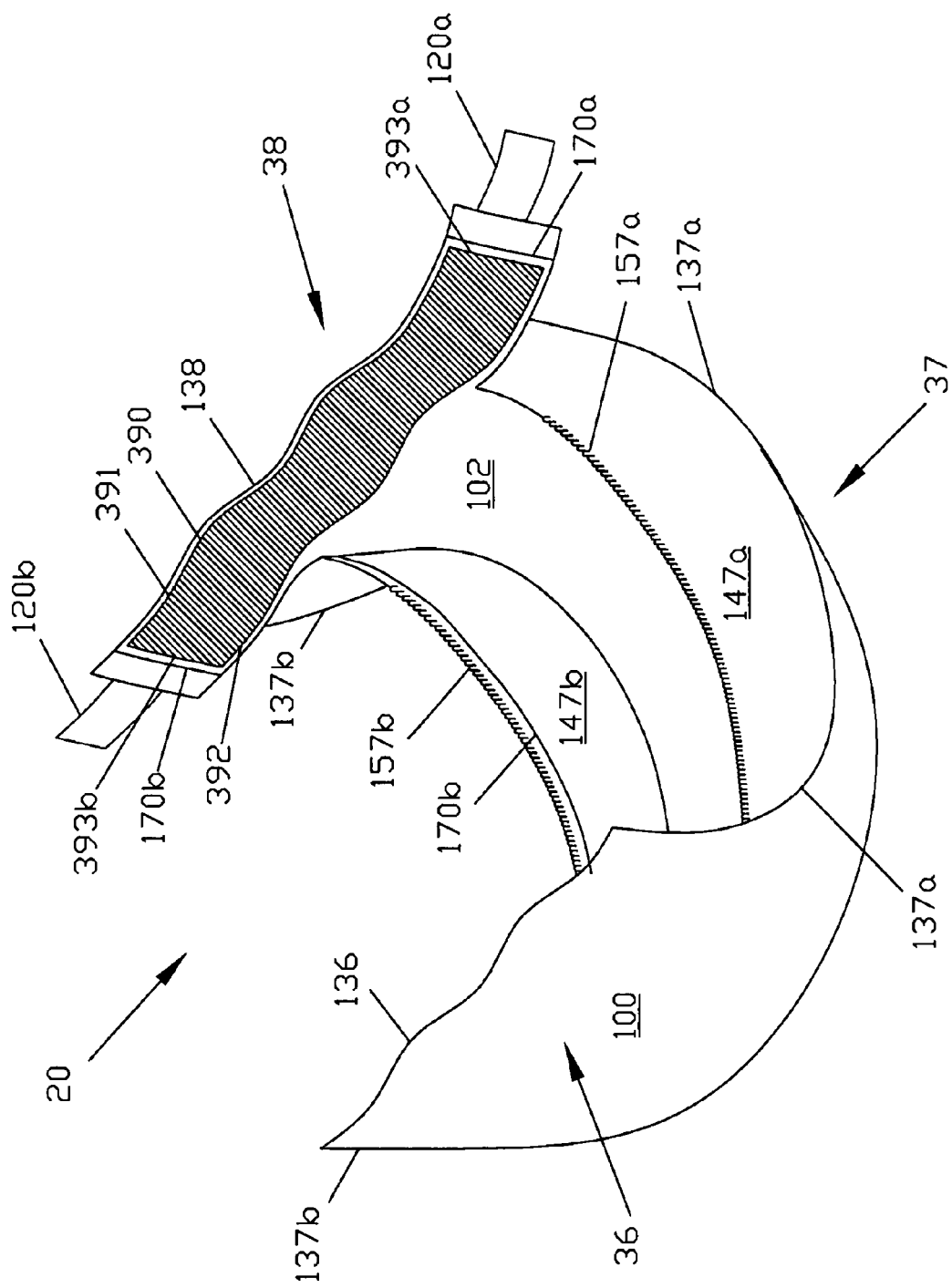
FIG. 10 is a perspective view of an exemplary diaper 20, which is shown in its relaxed, contracted state, i.e., with the contraction induced by elastic members. In this figure, the interior portion of the diaper 20 is shown facing upward.
Figure 11:
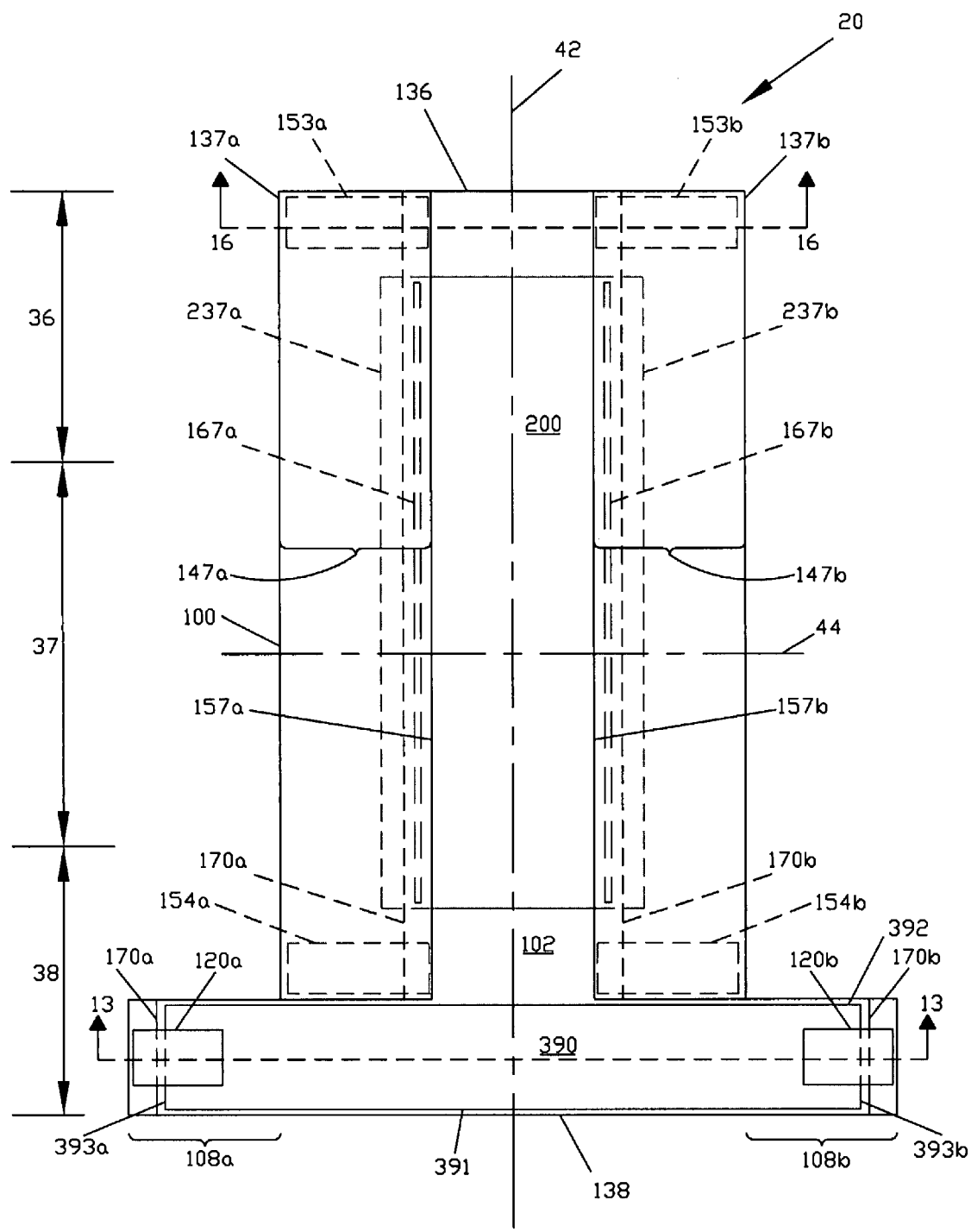
FIG. 11 is plan view of another exemplary diaper 20 showing an alternative form of fasteners.
Figure 12:
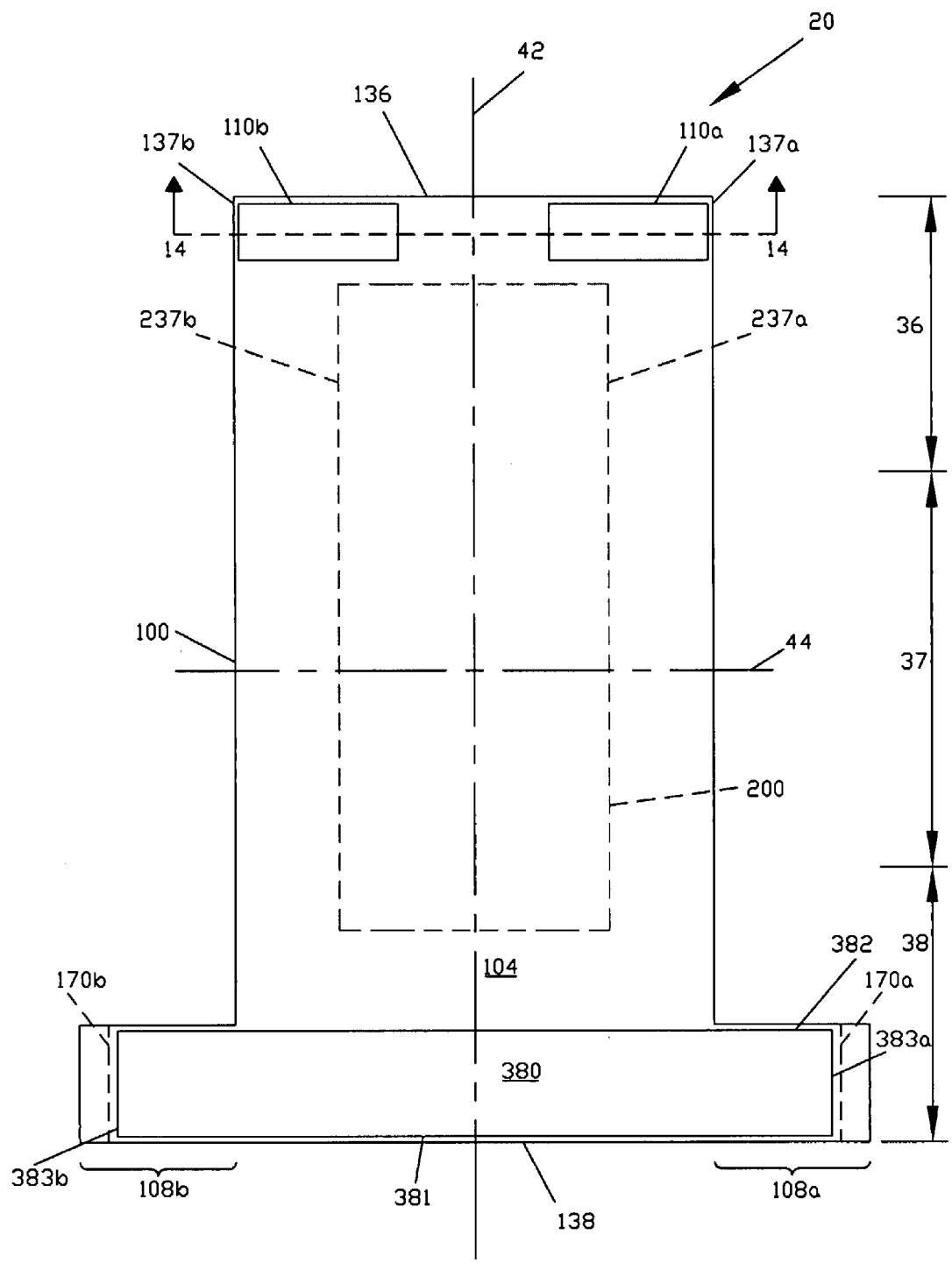
FIG. 12 is a plan view of the diaper 20 of FIG. 11 with the exterior portion of the diaper 20 shown facing the viewer.
Figure 13:
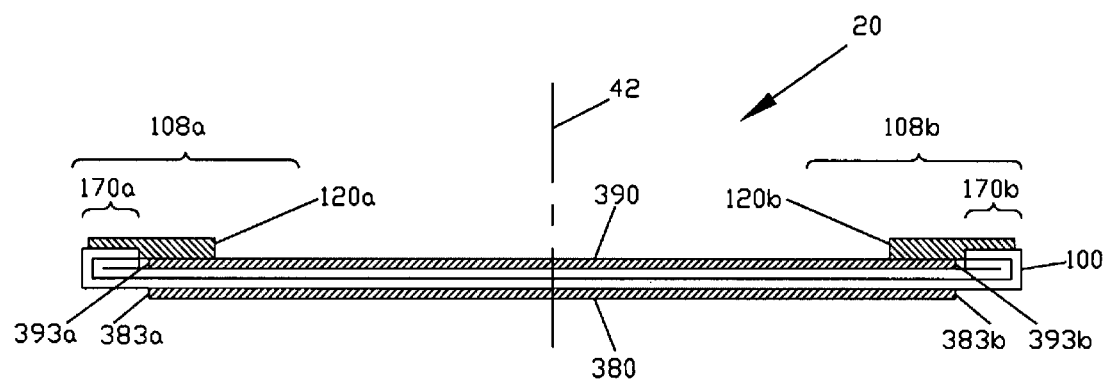
FIG. 13 is a section view of the diaper 20 of FIGS. 11 and 12 taken at the section line 13-13.
Figure 14:
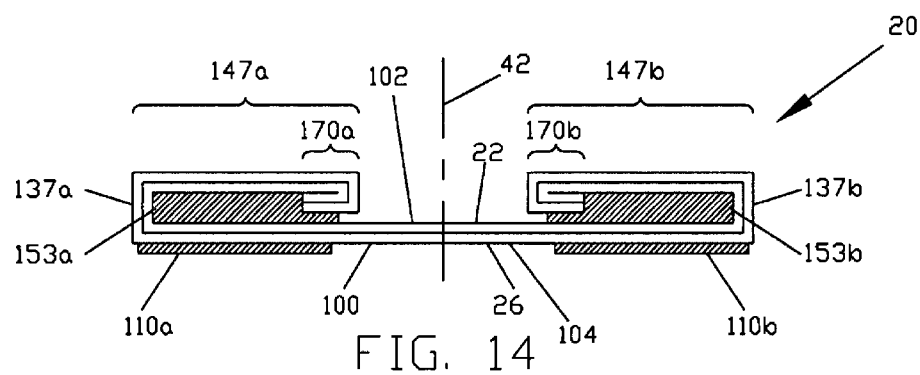
FIG. 14 is a section view of the diaper 20 of FIGS. 11 and 12 taken at the section line 14-14.

Between these attachment zones, the proximal edge 157 of each side flap 147 remains free, i.e., not attached to the interior surface 102 of the chassis 100 or to the absorbent assembly 200. Also between the attachment zones, and elastic strand 167 is attached adjacent to the proximal edge 157 of each side flap 147. Each elastic strand 167 is enclosed inside a hem 170 formed adjacent to the proximal edge 157 of each side flap 147. When stretched, the elastic strand 167 allows the adjacent side flap edge to extend to the flat uncontracted length of the chassis. When allowed to relax, the elastic strands 167 contract and gather the proximal edges 157, thereby lifting the side flaps 147 into position to serve as side barriers adjacent to the side edges 237 of the absorbent assembly 200, as shown in FIG. 8 and FIG. 10.

Figure 5:
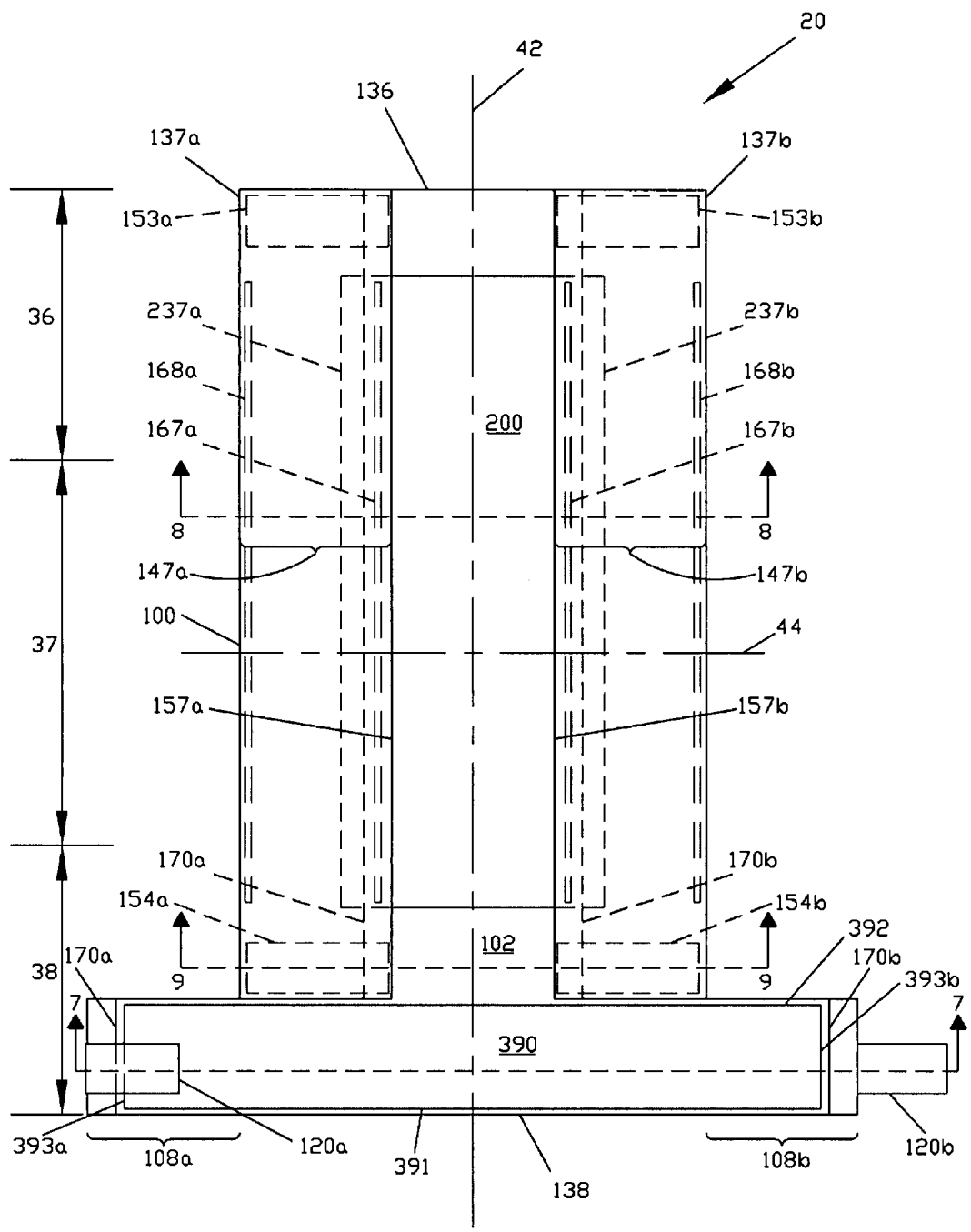
FIG. 5 is a plan view of the exemplary diaper 20 with two chassis ears extending laterally. In this figure, the interior portion of the diaper 20 is shown facing the viewer.
Figure 8:
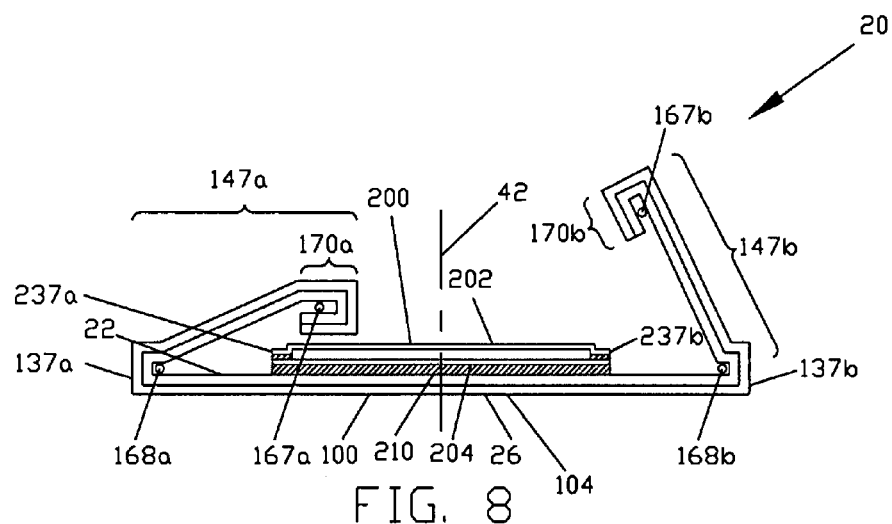
FIG. 8 is a section view of the diaper 20 of FIGS. 5 and 6 taken at the section line 8-8.

Another elastic strand 168 may be attached where the chassis 100 is folded to form the side flap 147, as shown in FIG. 5 and FIG. 8. When allowed to relax, this elastic strand 168 may gather the side edge 137 of the chassis 100 to form a side barrier at or adjacent to the side edge 137.

In the finished diaper, it is preferable that the chassis have side edges 137 that are not straight, but instead are notched, thereby giving an overall shape in plan view of a "T" or of an "I" to the diaper 20. Such a non-rectangular configuration may impart a tailored appearance to the diaper 20 when it is worn and may also impart an impression that the diaper 20 will fit comfortably between the legs of a wearer.

Figure 6:
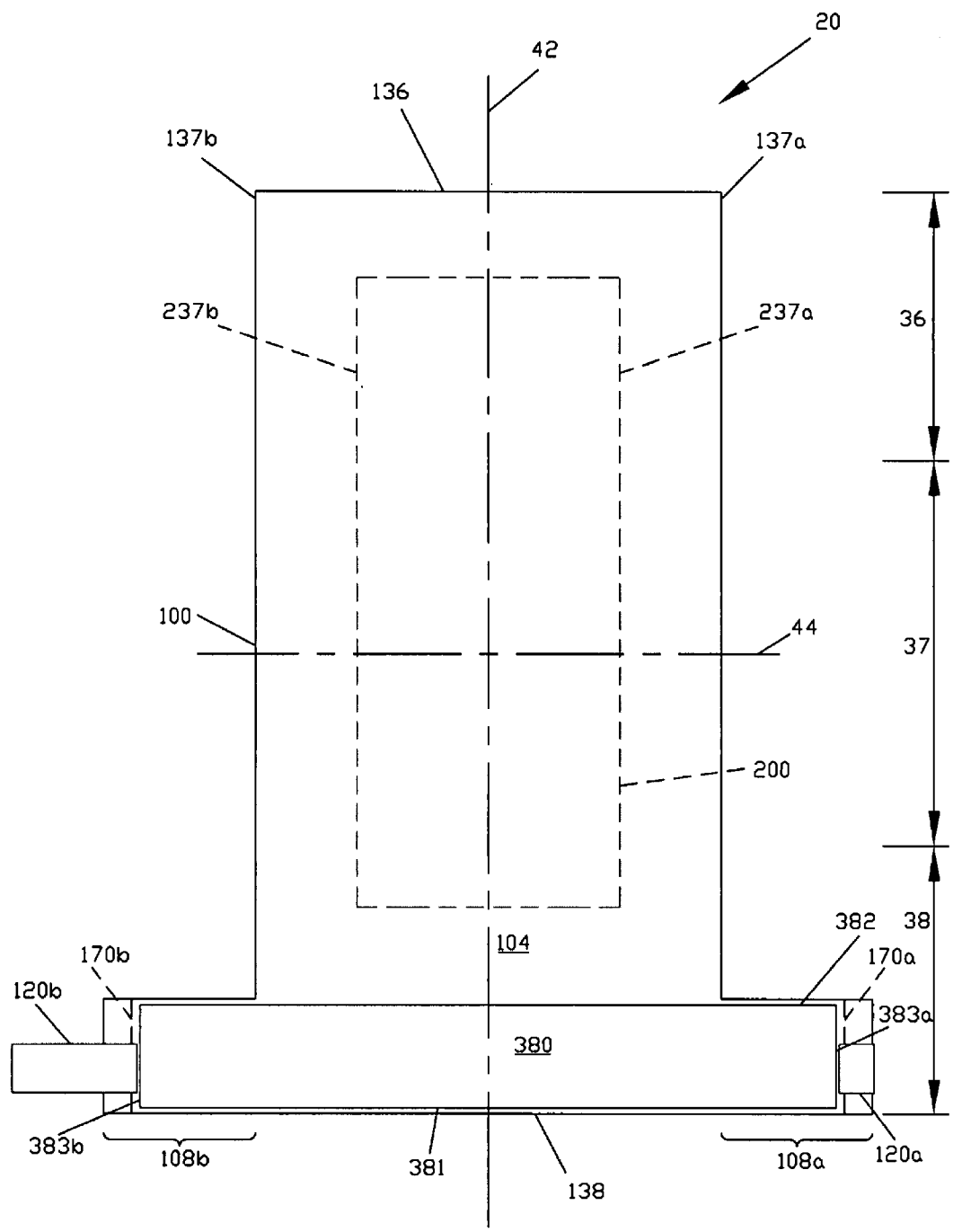
FIG. 6 is a plan view of the diaper 20 of FIG. 5 with the exterior portion of the diaper 20 shown facing the viewer.
Figure 24:
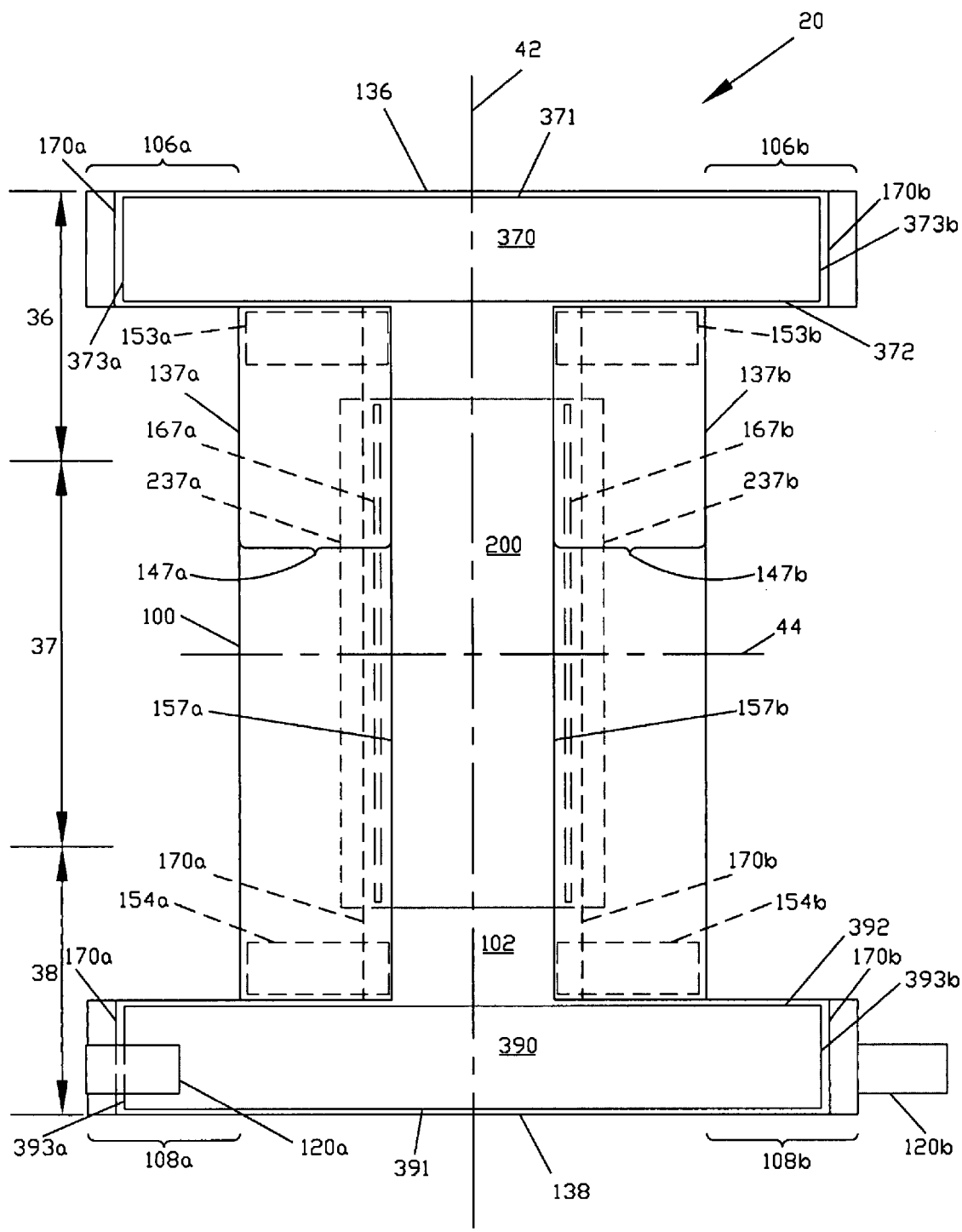
FIG. 24 is a section view of an exemplary diaper 20 with four chassis ears extending laterally. In this figure, the interior portion of the diaper 20 is shown facing the viewer.

An exemplary non-rectangular configuration of the chassis is shown in FIG. 5 and FIG. 6. As shown in these figures, laterally opposing portions 108 of the chassis 100 in the back waist region 138 may extend laterally outward while the adjacent side flaps 147 remain folded laterally inward. The laterally outwardly extending portions form a pair of back chassis "ears" 108 that impart a "T" shape to the diaper. Alternatively, laterally opposing portions of the chassis 100 in the front waist region 136 may extend laterally outward to form a pair of front chassis ears and thereby impart a "T" shape to the diaper. As another alternative, both front portions and back portions may extend laterally outward to form both a pair of front chassis ears 106 and a pair of back chassis ears 108 while the adjacent side flaps 147 remain folded laterally inward, in which configuration an "I" shape is imparted to the diaper 20, as shown in FIG. 24.

For ease of manufacturing and packaging, it is preferable that the chassis ears 106 and/or 108 remain folded laterally inward until a user desires to deploy them for use when applying the diaper 20 onto the body of a wearer. For this purpose, as shown in FIG. 1, one edge of each chassis ear may be defined by a frangible line of attachment 91 along which the chassis ear can be partially detached for deployment, i.e., for unfolding laterally outward. Such a frangible line of attachment may be formed in a layer or a laminate of layers by perforation, by the formation of a brittle area or areas at which the material will preferentially fracture when stressed, by the formation of a weaker area or areas at which the material will preferentially tear when stressed, by the formation of a friable area or areas at which the material will preferentially crumble when stressed and/or bent, or by any other method of providing frangibility that is suitable for the materials involved.

Figure 2:
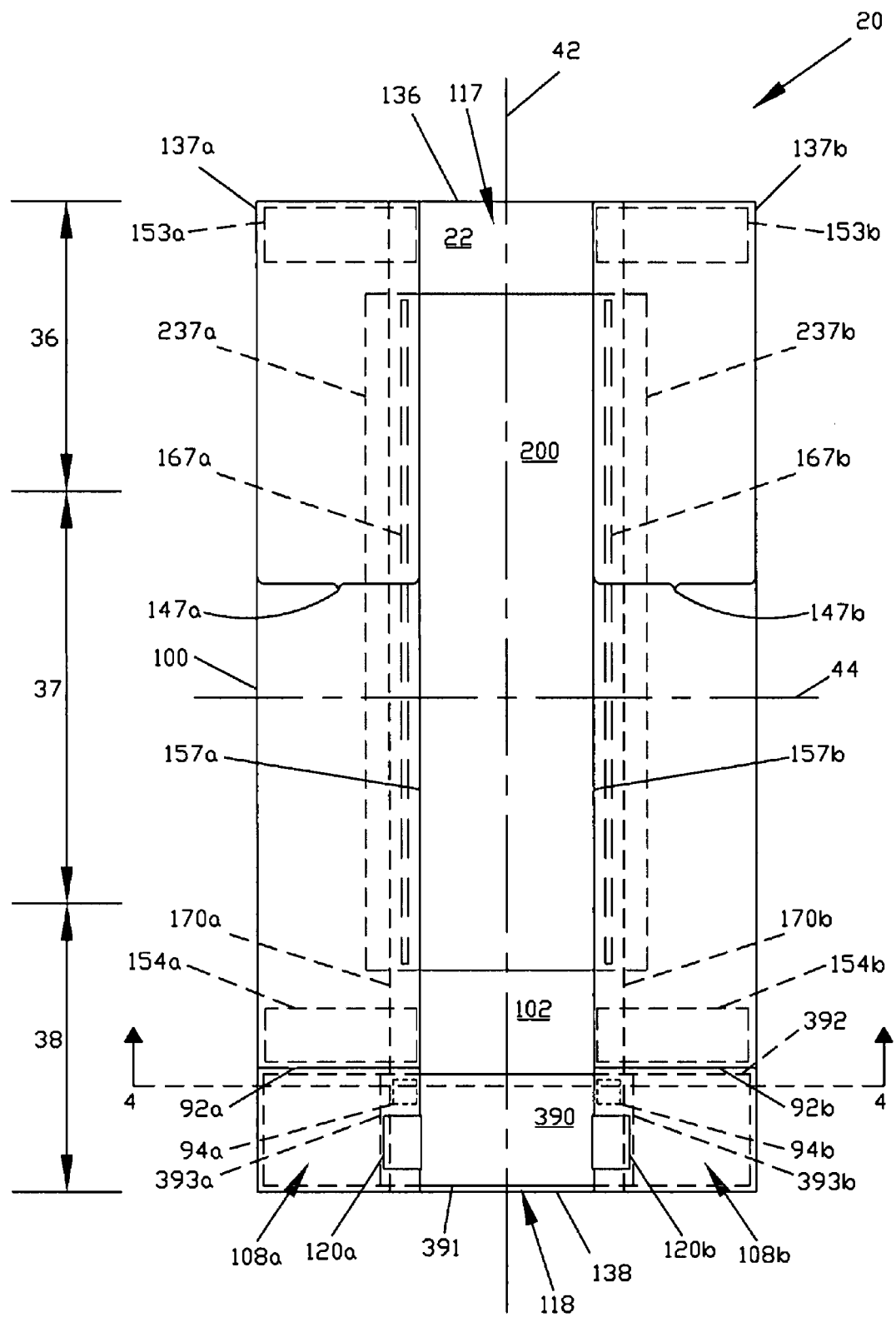
FIG. 2 is a plan view of another exemplary diaper 20 with the interior portion of the diaper 20 that faces inwardly toward the wearer shown facing the viewer.
Figure 4:
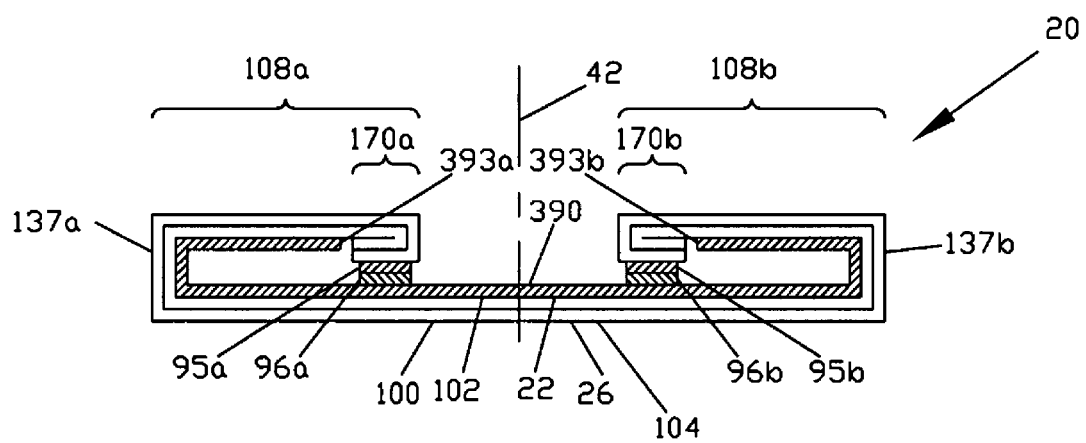
FIG. 4 is a section view of the diaper 20 of FIG. 2 taken at the section line 4-4.

Alternatively, as shown in FIG. 2, one edge of each chassis ear may be defined by a cut line 92 at which the chassis ear is severed from the adjacent side flap 147. Because the formation of this cut line could allow the chassis ear to unfold prematurely, the chassis ear may be held laterally inwardly folded by a releasable attachment member 94 until being deployed by being released and unfolded laterally outward so as to project laterally outward beyond the adjacent side flap. As shown in FIG. 4, the releasable attachment member 94 may include a releasable attachment element 95 disposed on the chassis ear and a complementary releasable attachment element 96 disposed on the interior surface underlying the chassis ear when it is laterally inwardly folded. Alternatively, a single attachment member disposed on either the chassis ear or the underlying interior surface may engage the material of the other surface releasably, thereby making a distinct complementary attachment member unnecessary, e.g., a hook member may engage a nonwoven material releasably. Such a releasable attachment member 94 may also be used in combination with a chassis ear that is defined by a frangible line of attachment 91 if additional assurance is desired that the chassis ear will not inadvertently be deployed prematurely.

As shown in the figures, each stretch waistband has a circumferentially extending longitudinally distal edge that is disposed adjacent to the respective waist edge of the chassis 100 and a longitudinally opposing circumferentially extending longitudinally proximal edge that is disposed relatively nearer to the lateral axis 44 than the longitudinally distal edge of the stretch waistband is disposed. Each stretch waistband also has laterally opposing longitudinally extending side edges, an interior surface, and an exterior surface.

Figure 7:
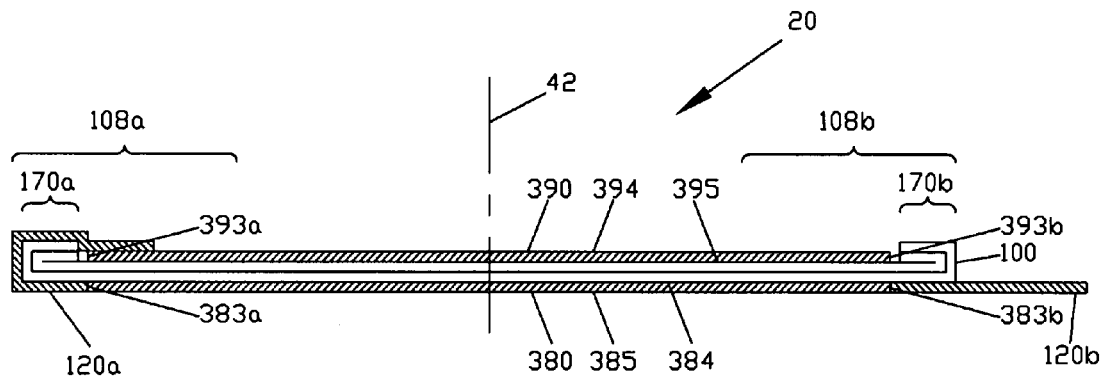
FIG. 7 is a section view of the diaper 20 of FIGS. 5 and 6 taken at the section line 7-7.

For example, the back interior stretch waistband 390 shown in FIG. 5 has a circumferentially extending longitudinally distal edge 391, a longitudinally opposing circumferentially extending longitudinally proximal edge 392, and laterally opposing longitudinally extending side edges 393. The interior surface 394 and the exterior surface 395 of this back interior stretch waistband 390 are identified in FIG. 7. Similarly, the back exterior stretch waistband 380 shown in FIG. 6 has a longitudinally distal edge 381, a longitudinally opposing proximal edge 382, laterally opposing side edges 383, an interior surface 384, and an exterior surface 385. As another example, the front interior stretch waistband 370 shown in FIG. 24 has a longitudinally distal edge 371, a longitudinally opposing proximal edge 372, and laterally opposing side edges 373.

Each of the stretch waistbands shown in the figures has a circumferential extent such that it overlies a portion of each of the paired chassis ears and extends continuously between them. For example, the back interior stretch waistband 390 shown in FIG. 5 overlies the majority of each of the back chassis ears 108 and extends across the back waist region 38 between these chassis ears 108. In particular, the side edges 393 of this back interior waistband 108 lie adjacent to and laterally inboard of the hems 170 of the chassis ears 108.

In some embodiments, a stretch waistband may have a relatively greater or a lesser circumferential extent than the stretch waistbands shown in the figures. For example, the side edges of a stretch waistband may lie laterally inboard of any fasteners disposed on the chassis ears, such as the fasteners 120 shown in FIG. 5. As another example, the side edges of a stretch waistband may lie relatively more distally than shown in the figures, such that the stretch waistband overlies substantially the entire lateral extents of the chassis ears.

The interior surface of an interior stretch waistband contacts the skin of the wearer when the diaper 20 is worn. Therefore, the layer forming the interior surface is preferably formed of a soft material that will not irritate the skin of the wearer. Many suitable materials are known in the art, including rayon and synthetic nonwovens, such as spunbonded or carded polypropylene, polyethylene, or polyester or other olefinic materials.

Figure 25:
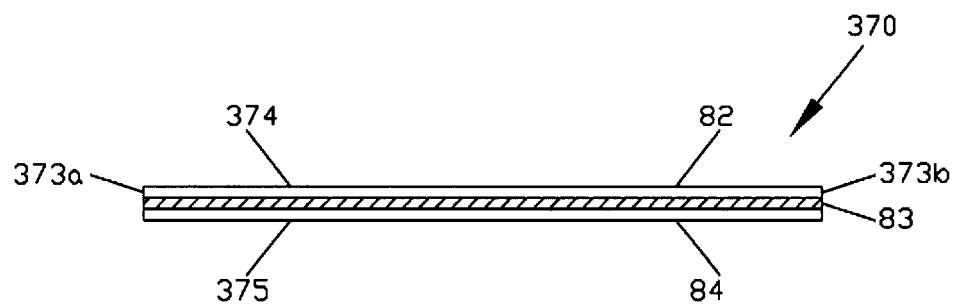
FIG. 25 is a section view of a laminate stretch waistband.

A stretch waistband may have a laminate structure. In particular, a stretch waistband may include an interior layer and a additional layer or layers disposed exteriorly of the interior layer. An elastic version of one of the aforementioned suitable materials such as, a nonwoven, exhibiting substantial elastic properties, may be used for any of the layers. For example, a front interior stretch waistband 370 having a laminate structure is shown in FIG. 25. This stretch waistband includes both an interior skin-contacting layer 82 and an elastic layer 83 laminated to the interior layer 82. Suitable materials for the elastic layer 83 are well-know in the art, including natural rubber strands, synthetic rubber stands, elastomeric films, etc. The material chosen for the elastic layer 83 preferably exhibits a force response proportional to its elongation. As shown in FIG. 25, a stretch waistband may also include an exterior cover layer 84 laminated to the elastic layer 83 on its surface opposite the interior layer 82, thereby forming a trilaminate in which the elastic layer 83 is sandwiched between the interior layer 82 and the exterior cover layer 84.

The layers of a stretch waistband may be laminated by any method(s) suitable for the elements being attached together and their constituent materials. For example, the elastic layer 83 may be maintained in a stretched condition while being attached to a relaxed interior layer 82 (and a relaxed exterior cover layer 84 if present) and then allowed to relax. The resultant contraction of the elastic layer 83 may gather the interior layer 82 in such a way as to create rugosities and the laminate thus formed may be extended in the direction of the original stretch up to the original dimension of the interior layer 82 (and the exterior cover layer 84 if present) with only the elastic layer 83 resisting the extension. A similar result may be achieved by, for example, first gathering the interior layer 82 (and the exterior cover layer 84 if present), such as by pleating it, and then attaching the elastic layer 83 in a relaxed condition. The resultant laminate may be extended in a direction perpendicular to the pleat ridges up to the original dimension of the interior layer 82 (and the exterior cover layer 84 if present) with only the elastic layer 83 resisting the extension.

Figure 26:
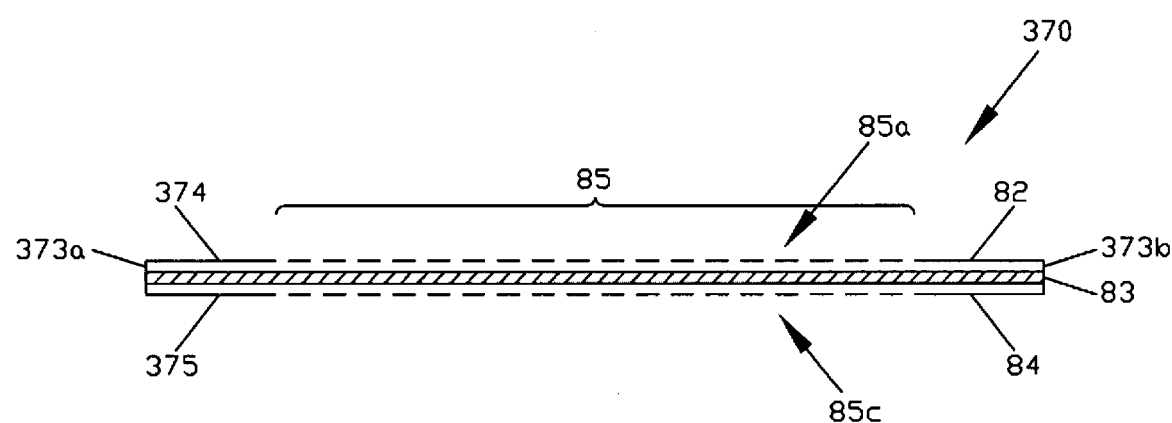
FIG. 26 is a view of the laminate stretch waistband of FIG. 25 in stretched condition.

In some exemplary methods, the lamination may be performed with both the elastic layer 83 and the interior layer 82 (and the exterior cover layer 84 if present) relaxed. All or a portion of the resultant laminate stretch waistband may subsequently be "activated" by subjecting it to elongation to create localized ruptures in a portion 85a of the interior layer 82 (and a portion 85c of the exterior cover layer 84 if present). In FIG. 26, the front interior stretch waistband 370 of FIG. 25 having such an activated portion 85 is shown in a stretched condition. The ruptured portion 85a of the interior layer 82 and the ruptured portion 85c of the exterior cover layer 84 are shown in dashed lines representing exemplary breaks in and/or separation of the fibers in nonwoven materials. The ruptured portion 85a of the interior layer 82 (and the ruptured portion 85c of the exterior cover layer 84 if present) in the resultant activated portion 85 of the laminate provides little or no resistance to extension in the direction of the original elongation. For example, when a nonwoven is used for the interior layer 82 (and the exterior cover layer 84 if present), the ruptured portion(s) typically include(s) breaks in and/or separation of the fibers that render the ruptured potion(s) substantially incapable of transmitting tensile forces in the plane of the nonwoven. Some suitable activation methods are known in the art as "ring-rolling" processes.

A stretch waistband may have uniform extension characteristics throughout its area or may have different extension characteristics in different portions. For example, a portion of a stretch waistband may be made laterally extensible to a maximum extensibility greater than a maximum extensibility of an adjacent portion, such that a desired fit on a wearer can be achieved. The difference in extensibility may be provided by varying the lamination process, for example by varying the localized elongation in an activation process.

Portions of the diaper 20 can be fastened together to encircle the waist and the legs of the wearer in many well-known ways. For example, separate fastening devices such as safety pins, separate tapes, a separate tie straps or straps, and/or a separate belt can be used for this purpose. Alternatively or in addition, fastening elements can be incorporated into the chassis 100 to enable a user to apply the diaper 20 to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. When configured for use, these incorporated fastening elements may project laterally or longitudinally outward or they may lie entirely inside the edges of the diaper 20.

For example, laterally opposing fastening elements may be attached to the chassis ears. The fastening elements 120 shown in the figures are disposed on the back chassis ear 108 and may be used to fasten the back waist region 38 to the front waist region 36 in a back-over-front manner. Alternatively, similar fastening elements may be disposed on front chassis ears 106 and used to fasten the front waist region 36 to the back waist region 38 in a front-over-back manner. As yet another alternative, similar fastening elements may be disposed on a waist region not having chassis ears extending from it and may be used to attach that waist region to chassis ears extending from the opposing waist region.

Figure 3:
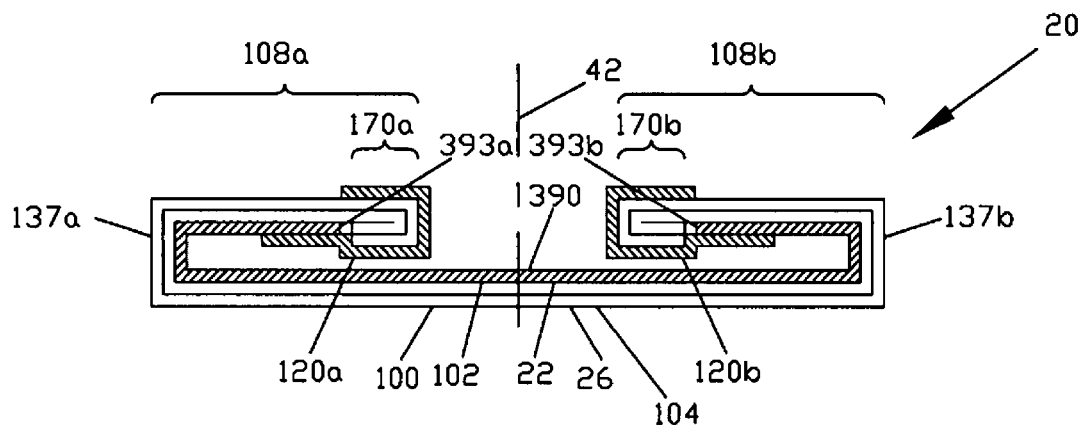
FIG. 3 is a section view of the diaper 20 of FIG. 1 taken at the section line 3-3.

The fastening elements 120 shown in FIG. 5 and FIG. 6 project laterally outward from the chassis ears 108 in the form of tapes. Such tapes may be coated with an adhesive. In order to prevent their premature adhesion to a surface, such adhesive tape fastening elements are typically folded over to prevent exposure of the adhesive and subsequently unfolded to expose the adhesive for use. For example, in FIG. 3, both fastening elements 120 are shown folded, while in FIG. 5, FIG. 6, and FIG. 7, the left fastening element 120a is shown still folded and the right fastening element 120b is shown unfolded and thereby configured for use.

Optionally, a fastening sheet (not shown) may be attached onto the exterior surface 104 of the chassis 100, as described in U.S. Patent Application Publication No. 2005/0171499A1. When a fastening sheet is provided, adhesive fastening elements may be adhered to the fastening sheet to fasten the back waist region 38 and the front waist region 36 together, or mechanical fastening elements may engage with it for the same purpose. The incorporation of such a fastening sheet may be desirable, for example, in order to make it possible to use a relatively inexpensive and relatively weak material for the backsheet 26.

Complementary fastening elements, such as those described in U.S. Patent Application Publication No. 2005/0171499A1, may likewise be used. For example, as shown in FIG. 11, FIG. 12, FIG. 13, and FIG. 14, back fastening elements 120 may be disposed on back chassis ears 108 and complementary front fastening elements 110 may be disposed in the front waist region 36. Suitable complementary fastening elements may be formed from cohesive fastening patches, mechanical fasters such as hooks and loops, or other known fastening elements.

Figure 15:
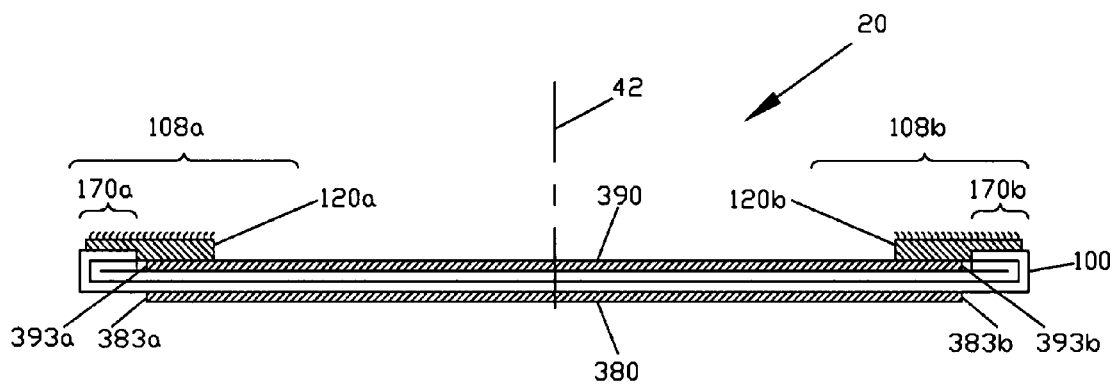
FIG. 15 is a section view of another exemplary diaper 20 taken at a section line similar to 13-13 and showing an alternative form of fasteners.

Alternatively, when a laminate backsheet is used and is oriented with the nonwoven disposed exteriorly, some forms of mechanical fasteners that typically require specific mating fastener elements, such as hooks that typically mate with loops, may be configured to engage with the nonwoven and thereby make the inclusion of the specific mating fastener element unnecessary. For example, as shown in FIG. 15, the fastening elements 120 may be formed by hook fastening patches configured to engage with the nonwoven layer 31 of the laminate backsheet 26. Such hook fastening elements may be disposed similarly to the cohesive fastening patch fastening elements shown in FIG. 13.

As described in U.S. Patent Application Publication. No. 2005/0171499A1, a portion or the whole of the chassis 100 may be made extensible to a degree greater than the inherent extensibility of the material or materials from which the chassis is made, e.g., the backsheet 26, the inner liner 22, or both. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to encircle the waist of an individual wearer whose waist circumference falls within a predefined range, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to fit a wearer who is larger than the unextended smaller diaper would fit. In other words, a lesser amount of material is needed in order to make a diaper capable of being properly fitted onto a given size of a wearer when the material is made extensible as described.

Figure 17:
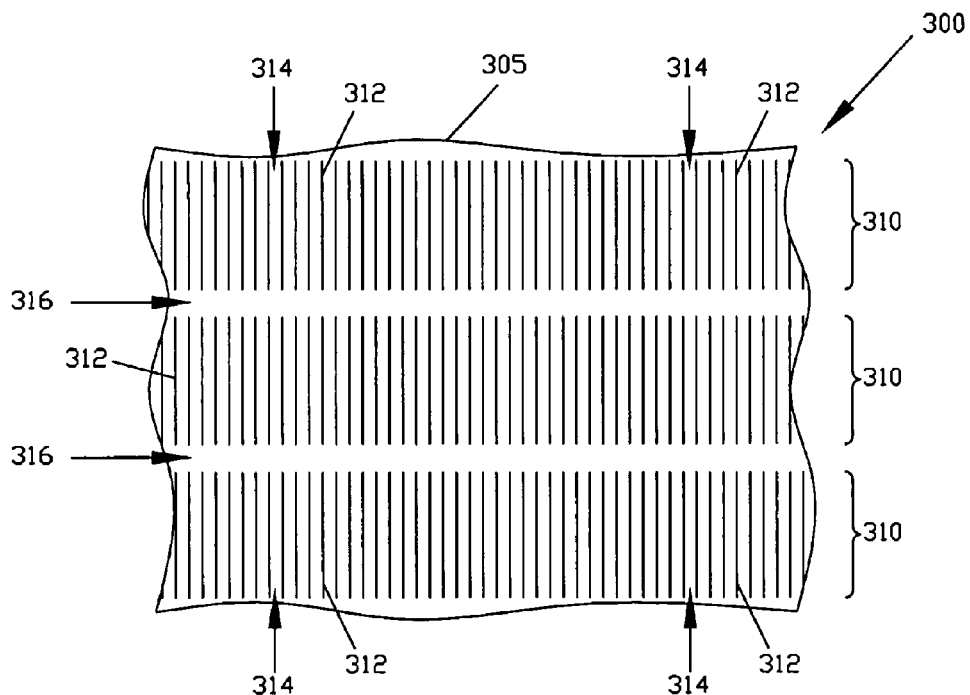
FIG. 17 is a plan view of an exemplary fragment of a formed web material.
Figure 18:
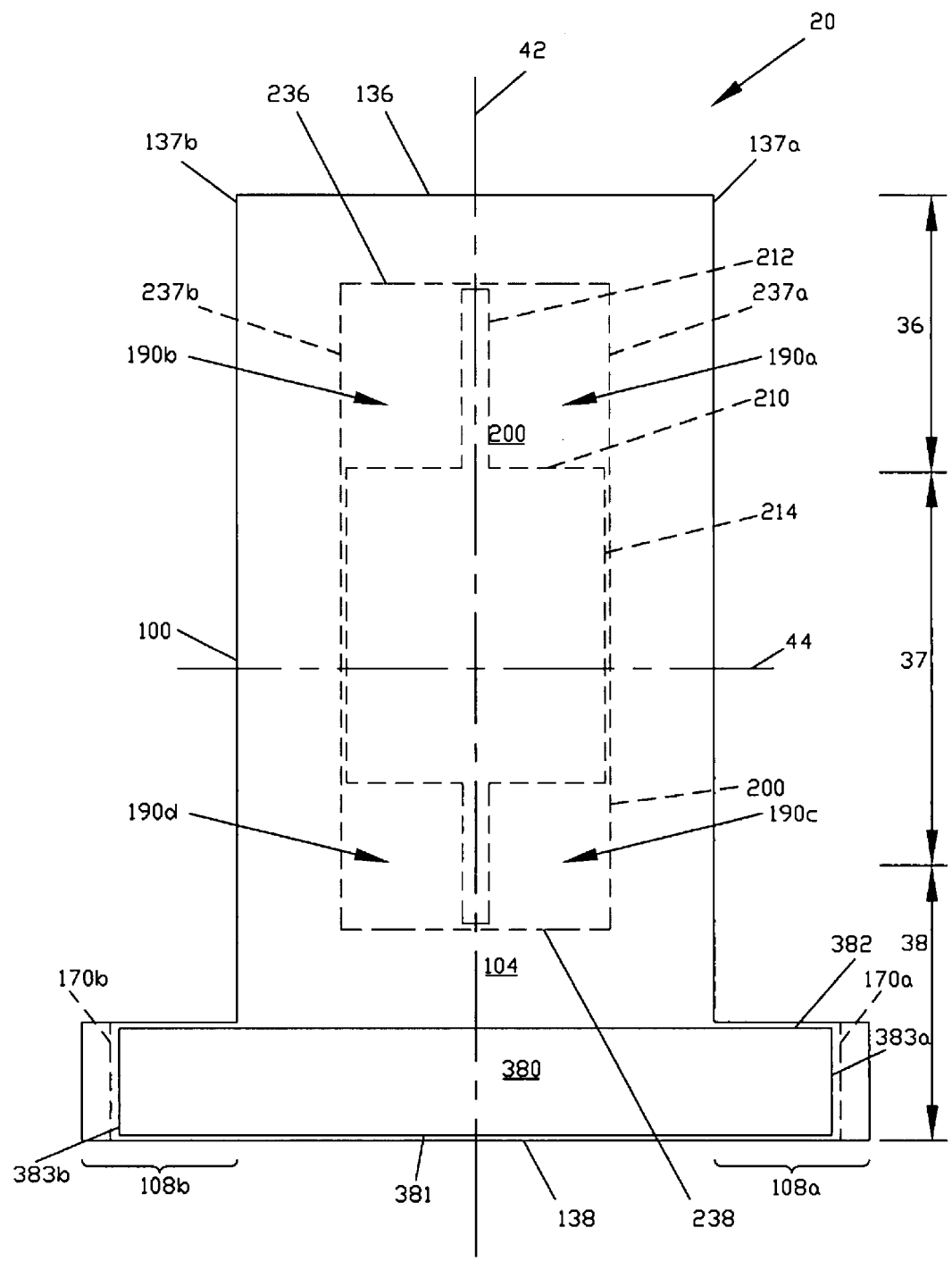
FIG. 18 is a simplified plan view of an exemplary diaper 20, which is shown in its flat, uncontracted state, i.e., without the contraction induced by elastic members, having the absorbent assembly attached to the chassis in a cruciform attachment pattern. In this figure, the exterior portion of the diaper 20 is shown facing the viewer.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801. An exemplary fragment 300 of such a formed web material 305 is shown in FIG. 17. This formed web material 305 includes distinct laterally extending regions 310 in which the original material has been altered by embossing or another method of deformation to create a pattern of generally longitudinally oriented alternating ridges 312 and valleys 314 in the web. The formed web material 305 also include laterally extending unaltered regions 316 located between the laterally extending altered regions 310. The formed web material can be extended in a direction perpendicular to the ridges, up to the point where the ridges and valleys flatten, with substantially less force than is required to extend beyond that point. Thus, such formed web materials exhibit an extensible behavior resembling that of traditional elastic materials, but may be made of relatively less expensive materials that are not inherently elastic and, thus, their use may provide an advantage in terms of the cost of manufacturing the absorbent articles.

The front laterally central portion 117 and/or the back laterally central portion 118 of the chassis 100 may have a different range of extensibility from the portions of the chassis in the attachment zones 153 and 154 where the side flaps 147 are attached to the interior surface 102 of the chassis. Additionally or alternatively, either or both or the laterally central portions 117 and 118 may be extensible to a greater or lesser degree when subjected to a given level of opposing tensile forces, i.e., may be more easily or less easily extensible, than the portion of the chassis in the attachment zones. Similarly, the altered regions in the laterally central portions of the chassis may be deformed to a greater or a lesser degree than the altered regions in the attachment zones to render the laterally central portions more easily or less easily extensible than the respective portions in the attachment zones.

The portion of the chassis 100 underlying the stretch waistband may be made laterally extensible to a maximum extensibility greater than a maximum extensibility of an adjacent portion of the chassis, such that a lateral extension of each of the portions to its maximum extensibility facilitates application of the diaper 20 onto the body of a wearer by allowing the waist regions to be fitted properly to the wearer's waist. In particular, the area underlying and/or adjacent to the stretch waistband may be made more highly extensible than other regions of the chassis maximize the allowable range of extension of the stretch waistband.

As shown in FIG. 19, FIG. 20, FIG. 21, and FIG. 22, the absorbent assembly 200 includes an absorbent core 250. The absorbent core 250 has a laterally extending front edge 256, a longitudinally opposing back edge 258, a left side edge 257a, and a laterally opposing right side edge 257b. Any or all of the edges of the absorbent core 250 may lie inward of, or may coincide with, the respective edges of the absorbent assembly 200. For example, in the exemplary absorbent assembly 200 shown in FIG. 19, the side edges 257 of the absorbent core 250 are located laterally inward of the side edges 237 of the absorbent assembly 200, while ht front edge 256 and back edge 258 of the absorbent core 250 coincide with the respective front edge 236 and back edge 238 of the absorbent assembly 200.

The absorbent assembly 200 may be attached to the chassis 100 over any part or the whole of the area of the absorbent assembly 200. Preferably, the absorbent assembly 200 is attached on its exterior surface 204 to the chassis 100 is a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern. Within the extend of the cruciform attachment pattern 210, the absorbent assembly 200 may be attached to the chassis 100 continuously or intermittently, such as in the form of dots, stripes, beads, spirals, etc.

An exemplary contiguous cruciform attachment pattern 210 is shown in FIG. 18, FIG. 19, FIG. 20, FIG. 21, and FIG. 22. The portions 190 of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIG. 18, FIG. 19, and FIG. 21 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIG. 18, FIG. 19, FIG. 20, and FIG. 22 prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness of the side flaps 147 when the elastic strands 167 lift the proximal edges 157 into contact with the body of the wearer, by supporting the crotch region 37 and thereby preventing the side flaps 147 from distorting and failing to maintain contact with the body.

Figure 19:
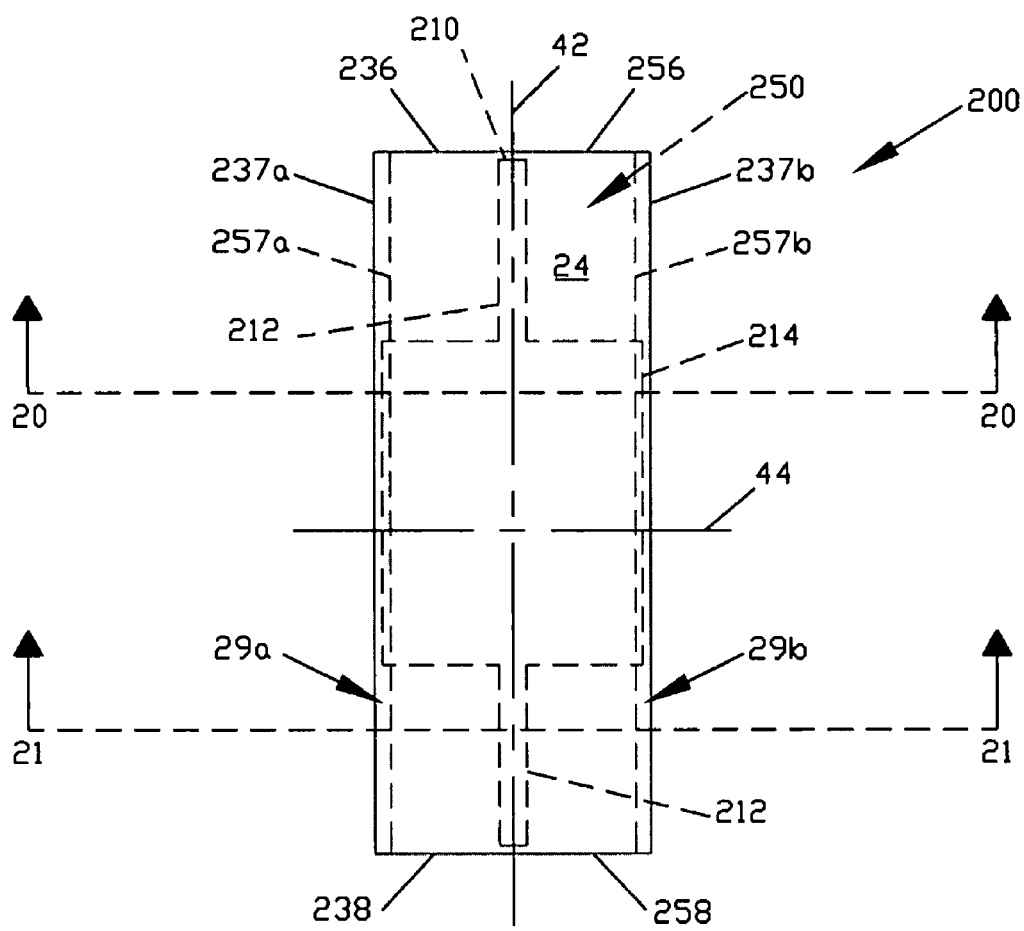
FIG. 19 is a plan view of an exemplary absorbent assembly 200. In this figure, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.
Figure 20:
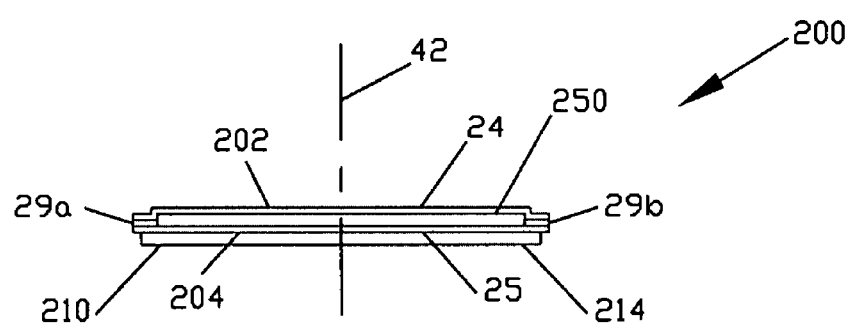
FIG. 20 is a section view of the absorbent assembly 200 of FIG. 19 taken at the section line 20-20.
Figure 21:
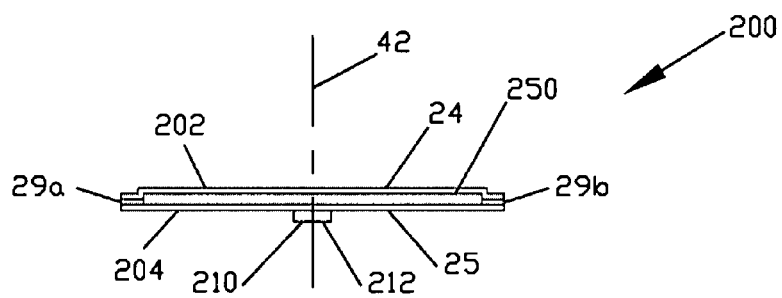
FIG. 21 is a section view of the absorbent assembly 200 of FIG. 19 taken at the section line 21-21.

The cruciform attachment pattern 210 may be disposed either symmetrically or asymmetrically with respect to either or both of the longitudinal axis 42 and the lateral axis 44 of the chassis 100. For example, the cruciform attachment pattern 210 shown in FIG. 19 is disposed symmetrically with respect to the longitudinal axis 42 and asymmetrically offset toward the front waist region 36 relative to the lateral axis 44. In addition, the cruciform attachment pattern 210 may be disposed symmetrically or asymmetrically with respect to either or both of the side edges 237 and the front edge 236 and the back edge 238 of the absorbent assembly 200. Suitable configurations of cruciform attachment patterns are disclosed in U.S. Pat. No. 6,962,578.

The absorbent core 250 may be disposed between a lower covering sheet that is disposed on the exterior face of the absorbent core 250 in a face-to-face arrangement with the interior surface 102 of the chassis and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in the figures, an upper covering sheet 24 and a lower covering sheet 25 are attached together at or adjacent to the side edges 237 of the absorbent assembly 200 in adhesive attachment zones 29. Alternatively, the upper covering sheet 24 and the lower covering sheet 25 may be attached together in places other than the side edges 237 of the absorbent assembly 200, e.g., at or adjacent to the end edges 236 and 238, or at or adjacent to both the end edges 236 and 238 and the side edges 237.

The upper covering sheet 24 is water-permeable and allows liquid waste to pass through to the absorbent core 250, where the liquid waste is absorbed. The lower covering sheet 25 may be water-impermeable, but is preferably water-permeable. The upper covering sheet 24 may form The interior surface 202 of the absorbent assembly 200 that is intended to be placed against the body of the wearer and therefore is preferably formed of a soft material that will not irritate the skin of the wearer. Many materials that are suitable for a water-permeable covering sheet are well-known in the art, including synthetic nonwovens such as spunbonded or carded polypropylene, polyester, or rayon.

Figure 22:
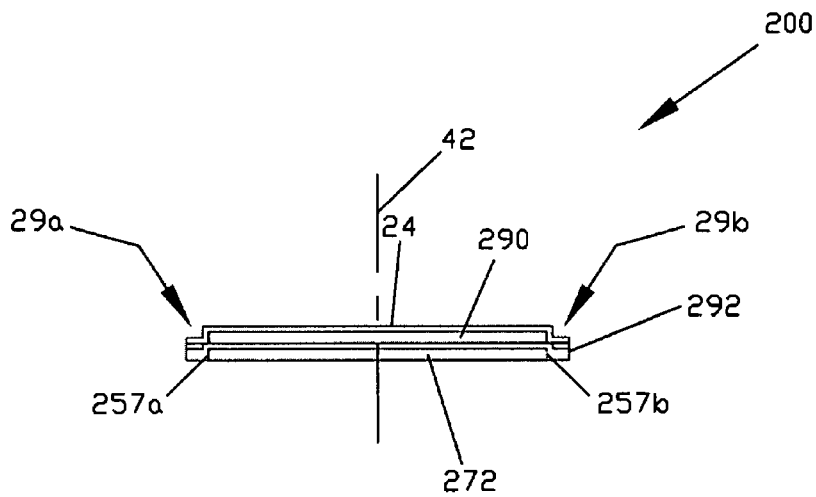
FIG. 22 is a section view of another exemplary absorbent assembly 200 taken at a section line similar to 20-20.

The absorbent core may include an acquisition component in addition to one or more storage components. The absorbent core acquisition component serves to acquire deposited liquid bodily waste material and transfer it to the absorbent core storage component. Preferred material for the acquisition component included synthetic fiber materials, open celled polymeric foam materials, fibrous nonwoven materials, cellulosic nonwoven materials, and various combination synthetic/cellulosic nonwoven materials. Examples of such acquisition materials are more fully described in U.S. Pat. No. 4,950,264. Such an absorbent core 250 including an acquisition component 290 overlying an absorbent core storage component 272 is shown in FIG. 22. A separation sheet 292 of, e.g., a tissue or a nonwoven material, may be disposed between the absorbent core storage component 272 and the absorbent core acquisition component 290 to help ensure that non of the gel formed by a superabsorbent polymer that may be included in the absorbent core storage component reaches the skin of the wearer.

Suitable well-known absorbent materials for the absorbent core include cellulose fibers in the form of comminuted wood pulp, which is commonly known as "airfelt", layers or sheets of natural or synthetic fibrous material, superabsorbent polymer, etc. These absorbent materials may be used separately or in combination and many may be used in a discrete form, i.e., in the form of fibers, granules, particles, layers and the like.

Figure 23:
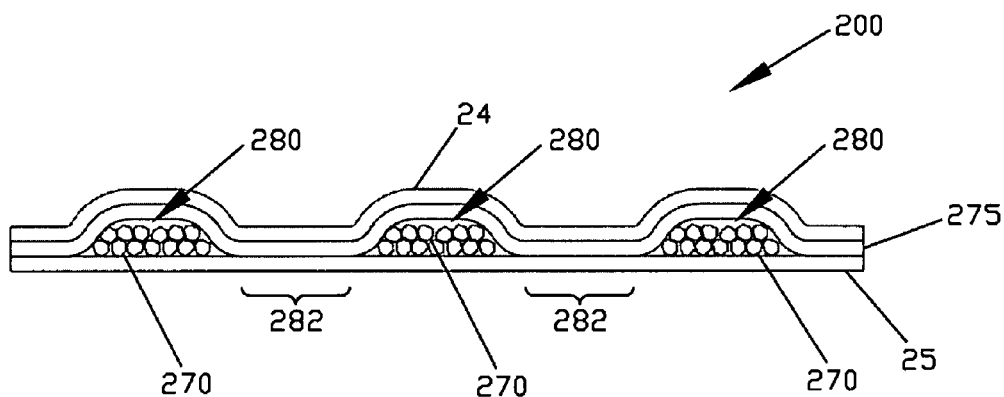
FIG. 23 is a section view of an exemplary absorbent core 250.

The discrete form of an absorbent material may be immobilized in pockets formed by a layer of thermoplastic material, such as a hot melt adhesive, that intermittently contacts and adheres to a substrate, such as a covering sheet, while diverging away from the substrate at the pockets. Absorbent assemblies having such pocket structures are described in detail in U.S. Patent Application Publications Nos. 2004/0167486 and 2004/0162536. An exemplary absorbent assembly 200 having such a structure is shown in FIG. 23. In this absorbent assembly 200, the absorbent core 250 includes particles of superabsorbent polymer 270 that are contained inside pockets 280 formed by a layer 275 of thermoplastic material. This absorbent core 250 contains no cellulose fibers. Alternatively, the absorbent core 250 may include both particles of superabsorbent polymer and airfelt and both materials may be contained inside the pockets. As shown in FIG. 23, the layer 275 of the thermoplastic material intermittently contacts and adheres to the lower covering sheet 25 at the area of attachment 282. Between the areas of attachment 282, the layer 275 diverges away from the lower covering sheet 25 to form the pockets 280. The layer 275 may have the form of a sheet of fibers of the thermoplastic materials through which the liquid waste may pass to the particles of superabsorbent polymer 270 to be absorbed. In FIG. 23, a separate upper covering sheet 24 is shown overlying the layer 275 of the thermoplastic material. Alternatively, the separate upper covering sheet 24 may be omitted and the layer 275 in the form of a fibrous sheet may server as the upper covering sheet 24.

The disclosures of all patents, patent applications and any patents which issue thereon, as well as any corresponding published foreign patent applications, and all publications listed and/or referenced in this description, are hereby incorporated in their entireties herein by reference. It is expressly not admitted that any of the documents or any combination of the documents incorporated herein by reference teaches or discloses the present invention. In the case of any conflict between the definitions of terms, the usage in this description overrides the conflicting usage in any incorporated reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising:

a chassis having a front waist region, a back waist region, and a crotch region between the waist regions, laterally opposing side edges defining its width, longitudinally opposing front and back waist end edges defining its length, an interior surface and an exterior surface; and an absorbent assembly attached to the interior surface of the chassis, the absorbent assembly having side edges and end edges disposed proximally relative to the respective side edges and end edges of the chassis, the chassis including a water-impermeable backsheet and laterally opposing side flaps formed by laterally inwardly folded portions of the chassis in at least the crotch region, each side flap being attached to the interior surface adjacent to its longitudinally distal ends and having a longitudinally extending elastic gathering member attached adjacent to its proximal edge, the chassis also including at least one pair of laterally opposing deployable chassis ears formed by laterally inwardly folded portions of the chassis in at least one of the waist regions, each chassis ear being held laterally inwardly folded by a frangible line of attachment until being deployed by being detached at the frangible line and unfolded laterally outward so as to project laterally outward beyond the respective side flap; and at least one stretch waistband attached to the chassis in at least one of the waist regions, the stretch waistband overlying at least a portion of each of the pair of chassis ears and extending continuously therebetween laterally, the stretch waistband providing a contractive force when the respective waist region is expanded laterally.

2. The disposable diaper of claim 1 wherein the stretch waistband includes a skin-contacting layer and an elastic layer laminated to the skin-contacting layer.

3. The disposable diaper of claim 1 wherein the stretch waistband comprises a trilaminate including an interior layer, an exterior cover layer, and an elastic layer sandwiched between the interior layer and the exterior cover layer.

4. The disposable diaper of claim 3 wherein the trilaminate includes an activated portion in which a ruptured portion of the interior layer and a ruptured portion of the exterior cover layer provide substantially no resistance to elongation and the elastic layer provides the contractive force.

5. The disposable diaper of claim 1 wherein the stretch waistband is attached to the chassis interiorly.

6. The disposable diaper of claim 1 wherein the stretch waistband is attached to the chassis exteriorly.

7. The disposable diaper of claim 1 wherein the absorbent assembly is attached to the chassis in a cruciform pattern of attachment having a longitudinally extending portion intersecting a laterally extending portion.

8. The disposable diaper of claim 1 wherein the chassis comprises a formed web material including at least two distinct laterally extending embossed regions each containing a pattern of generally longitudinally oriented alternating ridges and valleys created by an embossment and also containing an unembossed region located between the embossed regions, such that the formed web material can be laterally extended to a given extent with the application of relatively less force than that required to laterally extend the same web material to the same given extent before the embossment.

9. The disposable diaper of claim 1 wherein the chassis includes two of the chassis ears in the back waist region and two of the chassis ears in the front waist region.

10. The disposable diaper of claim 9 comprising one of the stretch waistbands in the back waist region and one of the stretch waistbands in the front waist region.

11. The disposable diaper of claim 1 comprising two of the stretch waistbands.

12. The disposable diaper of claim 11 wherein one of the two stretch waistbands is disposed interiorly and the other of the two stretch waistbands is disposed exteriorly.

13. The disposable diaper of claim 12 wherein the two stretch waistbands are disposed in the same one of the waist regions.

14. A disposable diaper comprising:
a chassis having a front waist region, a back waist region, and a crotch region between the waist regions, laterally opposing side edges defining its width, longitudinally opposing front and back waist end edges defining its length, an interior surface and an exterior surface; and
an absorbent assembly attached to the interior surface of the chassis, the absorbent assembly having side edges and end edges disposed proximally relative to the respective side edges and end edges of the chassis,
the chassis including a water-impermeable backsheet and laterally opposing side flaps formed by laterally inwardly folded portions of the chassis in at least the crotch region, each side flap being attached to the interior surface adjacent to its longitudinally distal ends and having a longitudinally extending elastic gathering member attached adjacent to its proximal edge,
the chassis also including at least one pair of laterally opposing deployable chassis ears formed by laterally inwardly folded portions of the chassis in at least one of the waist regions, fastening elements being disposed on at least two of the chassis ears and adapted for fastening the front waist region to the back waist region to encircle a waist and legs of a wearer, each chassis ear being held laterally inwardly folded by a releasable attachment member until being deployed by being released at the attachment member and unfolded laterally outward so as to project laterally outward beyond the respective side flap; and
at least one stretch waistband attached to the chassis in at least one of the waist regions, the stretch waistband overlying at least a portion of each of the pair of chassis ears and extending continuously therebetween laterally, the stretch waistband providing a contractive force when the respective waist region is expanded laterally.

15. The disposable diaper of claim 14 wherein the releasable attachment member comprises an adhesive.

16. The disposable diaper of claim 14 wherein the releasable attachment member comprises complementary releasable attachment elements disposed respectively on the chassis ear and on the interior surface underlying the laterally inwardly folded chassis ear.

17. The disposable diaper of claim 14 wherein the releasable attachment member either is disposed on the chassis ear and is adapted to engage the interior surface underlying the laterally inwardly folded chassis ear, or is disposed on the interior surface underlying the laterally inwardly folded chassis ear and is adapted to engage the chassis ear, and to thereby hold the chassis ear laterally inwardly folded.

18. The disposable diaper of claim 14 wherein the chassis includes two of the chassis ears in the back waist region and two of the chassis ears in the front waist region.

19. The disposable diaper of claim 14 wherein the absorbent assembly is attached to the chassis in a cruciform pattern of attachment having a longitudinally extending portion intersecting a laterally extending portion.

20. A disposable diaper comprising:
a chassis having a front waist region, a back waist region, and a crotch region between the waist regions, laterally opposing side edges defining its width, longitudinally opposing front and back waist end edges defining its length, an interior surface and an exterior surface; and
an absorbent assembly attached to the interior surface of the chassis, the absorbent assembly having side edges and end edges disposed proximally relative to the respective side edges and end edges of the chassis,
the chassis including a water-impermeable backsheet and a nonwoven inner liner attached to the backsheet and forming a portion of the interior surface,
the chassis also including laterally opposing side flaps formed by laterally inwardly folded portions of the chassis in at least the crotch region, each side flap being attached to the interior surface adjacent to its longitudinally distal ends and having a longitudinally extending elastic gathering member attached adjacent to its proximal edge,
the chassis also including at least one pair of laterally opposing deployable chassis ears formed by laterally inwardly folded portions of the chassis in each of the waist regions, fastening elements being disposed on at least two of the chassis ears, the fastening elements comprising adhesive tapes and being adapted for fastening the front waist region to the back waist region to encircle a waist and legs of a wearer, each chassis ear being held laterally inwardly folded by a frangible line of attachment until being deployed by being detached at the frangible line and unfolded laterally outward so as to project laterally outward beyond the respective side flap; and
at least one stretch waistband attached to the chassis in at least one of the waist regions, the stretch waistband overlying at least a portion of each of the pair of chassis ears and extending continuously therebetween laterally, the stretch waistband providing a contractive force when the respective waist region is expanded laterally.

* * * * *